US011331270B2

(12) United States Patent
Temtsin-Krayz

(10) Patent No.: US 11,331,270 B2
(45) Date of Patent: *May 17, 2022

(54) DRY POWDER COMPOSITIONS FOR INTRANASAL DELIVERY

(71) Applicant: Formulex Pharma Innovations Ltd., Ness Ziona (IL)

(72) Inventor: Galia Temtsin-Krayz, Ness Ziona (IL)

(73) Assignee: Nasus Pharma Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/636,178

(22) PCT Filed: Aug. 19, 2018

(86) PCT No.: PCT/IL2018/050914
§ 371 (c)(1),
(2) Date: Feb. 3, 2020

(87) PCT Pub. No.: WO2019/038756
PCT Pub. Date: Feb. 28, 2019

(65) Prior Publication Data
US 2020/0368156 A1  Nov. 26, 2020

Related U.S. Application Data

(60) Provisional application No. 62/547,858, filed on Aug. 20, 2017.

(51) Int. Cl.
*A61K 9/00* (2006.01)
*A61K 31/485* (2006.01)
(Continued)

(52) U.S. Cl.
CPC .......... *A61K 9/0075* (2013.01); *A61K 9/0043* (2013.01); *A61K 9/0073* (2013.01);
(Continued)

(58) Field of Classification Search
None
See application file for complete search history.

(56) References Cited

U.S. PATENT DOCUMENTS 6,462,090 B1  10/2002  Slutsky et al.
6,866,039 B1   3/2005  Wright et al.
(Continued)

FOREIGN PATENT DOCUMENTS

EP  0588255 A1   3/1994
EP  2648788 A1  10/2013
(Continued)

OTHER PUBLICATIONS

Krieter, Phillip, et al., "Pharamacokinetics Properties and Human Use Characteristics of an FDA-Approved Intranasal Naloxone Product for the Treatment of Opioid Overdose", The Journal of Clinical Pharamacology, May 5, 2016.
(Continued)

*Primary Examiner* — Melissa S Mercier
(74) *Attorney, Agent, or Firm* — Banner & Witcoff, Ltd.

(57) ABSTRACT

The present application relates to a pharmaceutical composition in a form of dry powder for intranasal administration, comprising solid particles of at least one active agent and solid particles of a diluent, said pharmaceutical composition being substantially free of excipients other than the solid diluent, wherein said pharmaceutical composition having at least 90% of the particles of said at least one active agent with a mean particle size of 10-30 microns and less than 10% of the particles of said at least one active agent with a mean particle size equal to or below 5 microns. The particles of said diluent have a mean particle size of 30-200 microns. The present application also relates to an apparatus and
(Continued)

modified spray drying method for preparation of the pharmaceutical composition of the present invention in the dry powder form.

14 Claims, 16 Drawing Sheets

(51) Int. Cl.
*A61K 31/5517* (2006.01)
*A61K 47/26* (2006.01)
*A61K 47/10* (2017.01)
*A61K 47/38* (2006.01)
*A61K 45/06* (2006.01)

(52) U.S. Cl.
CPC ........ *A61K 31/485* (2013.01); *A61K 31/5517* (2013.01); *A61K 47/10* (2013.01); *A61K 47/26* (2013.01); *A61K 47/38* (2013.01); *A61K 45/06* (2013.01)

(56) References Cited

U.S. PATENT DOCUMENTS

| | | |
|---|---|---|
| 6,945,953 B2 | 9/2005 | Wright |
| 8,673,360 B2 | 3/2014 | Nagata et al. |
| 8,875,704 B2 | 11/2014 | Djupesland et al. |
| 9,211,253 B2 | 12/2015 | Crystal et al. |
| 9,556,260 B2 | 1/2017 | Frey, II et al. |
| 11,116,723 B2 * | 9/2021 | Temtsin-Krayz .... A61K 31/485 |
| 2001/0049391 A1 | 12/2001 | Alfonso et al. |
| 2003/0178440 A1 | 9/2003 | Wright |
| 2005/0028813 A1 | 2/2005 | Harrison |
| 2007/0119451 A1 | 5/2007 | Wang et al. |
| 2007/0178166 A1 * | 8/2007 | Bernstein ............ A61K 9/0073 424/499 |
| 2008/0292713 A1 | 11/2008 | Seville et al. |
| 2009/0041800 A1 | 2/2009 | Woiwode et al. |
| 2009/0246281 A1 | 10/2009 | Goller et al. |
| 2011/0033544 A1 | 2/2011 | Nagata et al. |
| 2012/0145150 A1 | 6/2012 | Donovan et al. |
| 2014/0073562 A1 | 3/2014 | Djupesland |
| 2015/0010633 A1 | 1/2015 | Li et al. |
| 2016/0220489 A1 | 8/2016 | Fleming et al. |
| 2016/0354288 A1 | 12/2016 | Uehara et al. |

FOREIGN PATENT DOCUMENTS

| | | |
|---|---|---|
| WO | 2009/050726 | 4/2009 |
| WO | 2016133863 A1 | 8/2016 |

OTHER PUBLICATIONS

Naloxone intranasal (Rx) Information Sheet, Medscape, available online Nov. 22, 2015.
Singh, Alok Pratap, et al., "SLN approach for nose-to-brain delivery of alprazolam", Drug Delivery and Translational Research, 2012, vol. 2, Issue 6, pp. 498-507.
Kosfeld, Michael, et al., "OxyContin increases trust in humans", Nature, vol. 435, Jun. 2, 2005, pp. 673-676.
Benedict, Christian, et al., "Intranasal Insulin to Improve Memory Function in Humans", Neuroendocrinology, 2007, vol. 86, pp. 136-142.
Freiherr, Jessica, et al., "Intranasal Insulin as a Treatment for Alzheimer's Disease: A Review of Basic Research and Clincial Evidence", CNS Drugs 2013, vol. 27, pp. 505-514.
Reger, M., et al., "Effect of intranasal insulin on cognition in memory impaired older adults: Modulation by APOE genotype", Neurobiology of Aging, 2006, vol. 27, pp. 451-458.
Jin, Kunlin, et al., "Cerebral Neurogensis Is Induced by Intranasal Administration of Growth Factors", Neurol. 2003, vol. 53, pp. 405-409.
Sherr, Jennifer, et al., "Glucagon Nasal Powder: A Promising Alternative to Intramuscular Glucagon in Youth with Type 1 Diabetes", Diabetes Care 2016, vol. 39, pp. 555-562.
Grassin-Delyle, Stanislas, et al., "Intranasal drug delivery: An efficient and non-invasive route for systemic administration: focus on opioids", Pharmacology & Therapeutics, 2012, vol. 134, pp. 366-379.
Operation Manual (Original), Mini Spray Dryer B-290 BUCHI Labortechnik AG, May 31, 2016, 82 pages.
Aundhia, C.J., et al., "Spray Drying in the Pharmaceutical Industry—A Review", Indo American Journal of Pharm Research. 2011:2(1), Jun. 15, 2011, pp. 125-138.
Goyal, Sandhya, et al., "Brain Targeting Through Nasal Route: An Overview on Transport Mechanism, Delivery Systems and Evaluation", 2013, World Journal of Pharmacy and Pharmaceutical Sciences, vol. 2, Issue 4, pp. 1607-1640.
EMA Guideline: Guideline on the Pharmaceutical Quality of Inhalation and Nasal Products, Jun. 2006, 27 pages.
Nasal Spray and Inhalation Solution, Suspension, and Spray Drug Products—Chemistry, Manufacturing, and Controls Documentation, Jul. 2002, 49 pages.
Obaidi, Mohammad, et al., "Improved Pharamacokinetics of Sumatriptan With Breath Powered Nasal Delivery of Sumatriptan Powder", Headache, 2013,vol. 53, pp. 1323-1333.
Fuseau, Eliane, et al., "Clinical Pharmacokinetics of Intranasal Sumatriptan", Clin Pharmacokinet., 2002, vol. 41(11), pp. 801-811.
FDA Guidance for Industry (Chemistry, Manufacturing & Controls Documentation): Metered-Dose Inhaler (MDI) & Dry Powder Inhaler (DPI) Drug Products—Quality Considerations (Apr. 2018), 50 pages.
"B-290 Mini Spray Dryer Operation Manual", BÜCHI Labortechnik AG, May 31, 2016.
Boström Emma et al, "In Vivo Blood-Brain Barrier Transport of Oxycodone in the Rat: Indications for Active Influx and Implications for Pharmacokinetics/Pharmacodynamics", Metabolism and Disposition, vol. 34, No. 9, (2006), 8 pages.

* cited by examiner

DRY POWDER COMPOSITIONS FOR INTRANASAL DELIVERY

TECHNICAL FIELD

The present application relates to delivery of drugs by intranasal administration of a pharmaceutical composition comprising at least one active agent and lactose or a lactose functional analogue as dry powder particles of specific particle size. The present application further relates to methods for the preparation of the pharmaceutical compositions and, more particularly, to methods of treatment of a subject in need thereof by administration of at least one pharmaceutical active agent via intranasal delivery to the uppermost region of the nasal cavity.

BACKGROUND

Intranasal delivery has a number of compelling advantages over other routes of administration, namely its non-invasiveness, rapid attainment of therapeutically relevant concentrations to the bloodstream, no first-pass metabolism, and ease of administration. Viable nasal delivery technologies have the potential to enable drug developers in creating innovative medicines using already approved products by delivering them through new routes of administration.

The intranasal delivery of drugs utilizes devices of several types, such as nebulizers, pressurized devices, dry powder sprayers, and bi-directional nasal devices. Dry powders are used in intranasal drug delivery due to many advantages of using this dosage form including the improved stability, administration of larger doses and lack of microbial growth (no need for preservatives). The administration of intranasal powders may improve patient compliance, especially if the smell and taste of the delivered composition comprising excipients is unpleasant. Compared to drug solutions, the administration of powders can result in a prolonged contact with the nasal mucosa. Powder form is suitable for delivery of both small molecules and biologics, especially peptides, hormones and antibodies.

Traditionally, intranasal preparations have been used for local administration of anti-histamines, decongestants and steroids, for alleviation of cold, allergy symptoms and/or nasal congestion. More recently, researchers' attention has been focused on two specific areas:

(1) The potential rapid drug absorption into the systemic circulation provided by turbinate and lymphoid tissues located at the back of the nasal cavity. This has already been in use in a number of indications e.g. migraine and pain relief, osteoporosis, vaccines, etc., and (2) The potential of the "Nose to Brain" (N2B) delivery to the central nervous system (CNS) presented by the olfactory region at the top of the nasal cavity, for the treatment of central nervous system (CNS) diseases. Blood brain barrier (BBB) prevents the treatment of neurological diseases by many potential drugs. Among them are Alzheimer's, Parkinson's, stroke, spinal cord injury, depression, and other CNS disorders. The blood-brain barrier is related primarily to the endothelium of the brain capillaries, through which few molecules can pass.

There are many advantages to the intranasal administration of medications that include, among others, a direct route to the blood stream, avoidance of hepatic first pass metabolism, higher bioavailability, ease and convenience of non-invasive manipulation, and proximity to the central nervous system. In addition, direct delivery of drugs to the brain provides the possibility of a better therapeutic-toxic ratio than with systemic drug delivery.

The olfactory region inside the nasal cavity, involved in sensing odors and chemicals, provides a unique and direct connection between the brain and the external environment. A number of studies reported drugs that do not or poorly cross the blood-brain barrier, but are rapidly delivered to the CNS when delivered intranasally, preferably delivered directly to the turbinate and lymphoid tissues located at the back of the nasal cavity. A free communication exists between the nasal submucosal interstitial space and the olfactory perineuronal space, which is contiguous with a subarachnoid extension that surroundings the olfactory nerve. The olfactory epithelium is capable of metabolizing some drugs. The olfactory neuronal pathway includes both the intracellular (intraneuronal) and extracellular (extraneuronal) pathway into the brain. After reaching the olfactory bulb and/or trigeminal region the actives may enter into other brain regions by diffusion, which may also be facilitated by arterial pulsation. In addition, intranasally administered drugs may also partially enter into CNS after its penetration into the systemic blood circulation.

Mostly hydrophilic drugs like dopamine and picolinic acid can be transported through the olfactory pathway. In case of lipophilic drugs, the systemic route is better than olfactory route because it can cross the blood brain barrier (BBB). Sinagh et al showed that alprazolam loaded in solid-lipid nanoparticles was rapidly transferred to the rabbit brain via intranasal route, bypassing the blood-brain barrier[1]. The enhanced rate and extent of transport may help in reducing the dose and dosing frequency, thereby providing a better compliance for ambulatory patients. Another study confirmed that intranasal oxytocin administration could increase confidence in human subjects[2].

[1] Alok Pratap Singh, Shailendra K. Saraf, Shubhini A. Saraf. SLN approach for nose-to-brain delivery of alprazolam, Drug delivery and Translational Research, 2012, vol. 2, Issue 6, pp 498-507
[2] Kosfeld M, Heinrichs M, Zak PJ, Fishbacher U, Fehr E: OxyContin increases trust in humans. Nature, 2005, vol. 435, pp 637-676

Moreover, an increasing number of studies on both animals and human subjects suggested that intranasal drug delivery could be used to transfer not only small molecules but also large sized biologics into the CNS by bypassing the BBB. Benedict et al showed that insulin administration by the intranasal route may improve memory and mood of healthy adults[3]. Freiherr et al[4] and Reger et al[5] demonstrated that the memory of AD patients may also be approved without altering blood levels of insulin or glucose. Jin et al reported that intranasal administration of either fibroblast growth factor-2 or heparin-binding epidermal growth factor may have potential as neurogenesis-promoting therapeutic agents[6]. All aforementioned pharmaceutical actives were administered to the nasal cavity as sprays.

[3] Benedict C, Hallshmid M, Schultes B, Born J, Kern W; Intranasal insulin to improve memory function in humans. Neuroendocrinology, 2007, vol. 86, pp136-142
[4] Freiherr J et al., Intranasal Insulin as a Treatment for Alzheimer's Disease: A Review of Basic Research and Clinical Evidence, CNS Drugs 2013, vol. 27, pp 505-514
[5] Reger MA, Watson GS, Frey WH 2$^{nd}$ et al., Effect of intranasal insulin on cognition in memory impaired older adults: modulation by APOE genotype. Neurobiol. Aging, 2006, vol. 27, pp 451-458
[6] Kunlin Jin MD, David A. Greenberg et al, Cerebral neurogenesis is induced by intranasal administration of growth factors; Ann. Neurol. 2003, vol. 53, pp 405-409

While intranasal delivery specifically to the olfactory region potentially provides a route for delivery of agents to the CNS, the olfactory region is difficult to access using conventional nasal delivery devices. The olfactory region is located in the uppermost region of the nasal cavity, where less than 10% of the inhaled air flows. Conventional nasal sprays deposit the majority of the drug in the lower region of the nasal cavity, with very little drug reaching the olfactory region Improved devices for the spray delivery to the olfactory region are described in US Patent Application No. 20070119451. The devices include a nosepiece and an elongated tubular member slidably disposed within the nosepiece for movement between a retracted position and an extended position. The tubular member is in flow communication with a reservoir containing the substance to be delivered. During the use, the tubular member extends from the device, to direct the substance toward the olfactory region. However, this reference does not disclose delivery of solid dry powders. Similar devices are disclosed in US 20030178440, U.S. Pat. Nos. 6,866,039, 6,945,953 and US 20050028813.

U.S. Pat. No. 9,556,260 described methods and compositions for the treatment of CNS disorders via intranasal administration of pooled human immunoglobulin G. As shown therein, intranasal administration allows the directed delivery of intact IgG to the brain bypassing the need to pass through the BBB. This results in greater efficiency for the treatment and reduces the necessary IgG dose that must be administered to achieve the desired effect. Whilst pooled human IgG is isolated from donated human plasma, pooled IgG is a limited resource. Therefore, if made possible, the reduction in the effective dose of IgG would effectively increase the therapeutic potential. Furthermore, intranasal administration of IgG nearly eliminates the systemic exposure caused by intravenous administration, improving the overall safety profile of the treatment. Also, it would be beneficial to intranasally administer IgG to the brain in the absence of permeability enhancers, some of which has neuro-stimulation effects themselves.

US Patent Application No. 20140073562 relates to a nasal delivery device and method of delivering a substance, preferably comprising oxytocin, non-peptide agonists thereof and antagonists thereof, preferably as one of a liquid, as a suspension or solution, or a powder to the nasal airway of a subject, preferably the posterior region of the nasal airway, and preferably the upper posterior region of the nasal airway which includes the olfactory bulb and the trigeminal nerve, and preferably in the treatment of neurological conditions and disorders.

U.S. Pat. No. 8,875,704 described a delivery device and method of delivering a powdered substance, in particular a triptan, such as sumatriptan, to the posterior region of a nasal cavity of a subject, in particular for the treatment of headaches, for example, cluster headaches and migraine, and neuropathic pain. WO 2016133863 provides a nasal powder formulation containing glucagon or a glucagon analog for nasal administration, useful in the treatment of hypoglycemia, and in particular the treatment of severe hypoglycemia. Sherr et al demonstrated in their clinical trials that glucagon nasal powder delivering glucagon transmucosally might be a promising alternative to intramuscular glucagon in adults and youth with type 1 diabetes[7]. However, Sherr et al did not mention that glucagon can be delivered from nose to brain.

[7] Jennifer L. Sherr et al, Glucagon Nasal Powder: A Promising Alternative to Intramuscular Glucagon in Youth with Type 1 Diabetes, Diabetes Care 2016; vol. 39, pp 555-562.

U.S. Pat. No. 6,462,090, US 20080292713, US 20150010633, US 20160354288 and other similar publications described dry powder inhalers (DPI) of therapeutic agents for pulmonary delivery. US 20150010633 disclosed the preparation of aerosol formulations of ondansetron useful exclusively for pulmonary delivery, because the active drug ondansetron, when administered by inhalation, must penetrate deep into the lungs in order to show physiological action. However, none of the publications above teach or mention the delivery of therapeutic agents to the brain via intranasal administration. Accordingly, there is an unmet need for methods of treating central nervous system (CNS) disorders with known and new active agents that provide specific targeting to the CNS (in terms of direct administration primarily to the brain), reduce systemic distribution of the active agents and lower the therapeutically effected doses needed for administration.

SUMMARY

The present application describes embodiments of a pharmaceutical composition in a form of dry powder for intranasal administration, comprising solid particles of at least one active agent and solid particles of a diluent, said pharmaceutical composition being substantially free of excipients other than the solid diluent, wherein said pharmaceutical composition having at least 90% of the particles of said at least one active agent with a mean particle size of 10-30 microns and less than 10% of the particles of said at least one active agent with a mean particle size equal to or below 5 microns. The particles of said diluent have a mean particle size of 30-200 microns.

The pharmaceutical composition of the embodiments of the present application comprises at least one hydrophilic active agent for intranasal delivery selected from analgesics, anti-emetics, anti-inflammatory agents, anti-bacterial agents, anti-viral agents, anti-depressants, anti-epileptics, anti-hypertensive agents, anti-migraine agents, anti-neoplastic agents, chemotherapeutic drugs, immunosuppressants, anti-Parkinsonian agents, anxiolytic agents, sedatives, hypnotics, neuroleptics, beta-blockers, corticosteroids, COX-2 inhibitors, opioid analgesics, protease inhibitors, hormones, peptides, antibodies, chemotherapy agents and mixtures thereof.

In some embodiments, the hydrophilic active agent may be selected from sumatriptan succinate, zolmitriptan salts, naratriptan, rizatriptan, almotriptan, eletriptan, frovatriptan, bupivacaine, fibroblast growth factor, cephalexin, lidocaine, clobazame, midazolam, alprazolam, diazepine, lorazepam, dexmedetomidine, monosialoganglioside, cocaine, insulin, glucagon, oxytocin, fentanyl, sulfentanil, diamorphine, ketamine, apomorphine, buprenorphine, morphine sulphate, oxycodone hydrochloride, butorphanol, NSAIDs, paracetamol, benzodiazepines, dopamine, pramipexole, rasagiline, rogitine, ondansetron, granisetron, metoclopramide, naloxone and naltrexone, atropine, epinephrine, isosorbide dinitrate, obitoxine, dexmedetomidine, metochlorpramide, L-dopa, nicotine, sildenafil, nafarelin, dobutamine, phenylephrine, tramazoline, xylometazoline, tramadol, methacholine, ipratropium, scopolamine, propranolol, verapamil, hydralazine, nitroglycerin, clofilium tosylatecannabis active compounds and pharmaceutically acceptable salts, isomers, and mixtures thereof.

In other embodiments, the pharmaceutical composition contains an acceptable diluent selected from lactose monohydrate, lactose, dextrose, sorbitol, mannitol, maltitol, xylitol or mixtures thereof.

The pharmaceutical composition of the embodiments is prepared by a modified spray drying method. An apparatus for the preparation of the pharmaceutical composition in the dry powder form of the embodiments comprises the following components:

a) A spray-drying chamber capable of spray-drying a clear and homogeneous solution of at least one active agent to obtain dry powder particles of said at least one active agent in a moist air, said solution being free of diluent;
b) A cyclone separator capable of receiving said dry powder particles and the moist air stream from said spray-drying chamber, separating said particles from the moist air through vortex separation, exhausting the air and transferring the separated particles to a receiving chamber through a bag filter; and
c) The receiving chamber pre-filled with a diluent and adapted for receiving the separated dry powder particles from the cyclone separator, stirring and homogenising said particles with the diluent to obtain the pharmaceutical composition in the dry powder form of the embodiments; wherein said diluent is capable of colliding and continuous in-situ blending with the particles during the stirring in the receiving chamber, thereby preventing their aggregation and preserving their original size and shape.

The spray-drying chamber is equipped with nozzles, which are used to produce droplets of the active agent solution, to control the droplet and powder particle size and to maximise heat transfer and the rate of solvent vaporisation. The droplet size may range from 20 to 180 μm, depending on a particular nozzle used. In the present embodiments, the sprayed solution of the active agent is free of any diluent. The nozzles are designed to spray the solution of the active agent into a hot air flow, thereby achieving a thorough mixing and uniform distribution of the hot air flow and sprayed solution in the spray-drying chamber to produce a substantially complete evaporation of liquids and drying of solid particles of the active agent from the mixture throughout said chamber.

At the laboratory scale, the stirring and homogenisation is achieved by using a magnetic stirrer and a magnetic bar of appropriate size, in addition to the rotation of the receiving chamber. At industrial scale, the stirring and homogenisation may be achieved by using a mechanical stirrer of appropriate size and form, or moving, rotation and vibration of the whole receiving chamber. A conventional spray-drying apparatus contains the empty receiving chamber collecting the dry powder particles of an active agent. This receiver is emptied from time to time in order to ensure the continuous process. In contrast, the present application discloses the receiving chamber pre-filled with a continuously stirred diluent for preventing aggregation of the dry powder particles and preserving their original size and shape.

The pharmaceutical composition of the embodiments contains a diluent added to the dry powder particles of the active agent after their spray-drying. In contrast, various pharmaceutical compositions described in the literature and processes commonly utilised for preparation of inhalable powders use surfactants and lipid agents for prevention of the particles aggregation and for the powder disaggregation and de-agglomeration. The use of a solid diluent, such as lactose or lactose functional analogues, having particles larger than the particles of the active agent, for the preparation of the inhalable dry powder formulation has never been mentioned in the literature.

In further embodiments, a method for the preparation of the pharmaceutical composition of the present application, comprises the following steps:
A. Preparing a clear and homogeneous solution of at least one active agent in an organic solvent or solvent mixture, in a solvent-water or water miscible solvent mixture, or in water.
B. Filling the receiving chamber with a diluent and continuously stirring the diluent in the receiving chamber;
C. Streaming the solution prepared in step (A) together with hot air or gas to the spray-draying chamber, spray-drying the solution in the spray-drying chamber to obtain dry powder particles of said at least one active agent in a moist air or gas, and transferring the obtained dry powder particles and the moist air or gas stream to the cyclone separator;
D. Separating said particles from the moist air or gas through vortex separation in the cyclone separator, exhausting the air or gas and transferring the separated particles to the receiving chamber through a bag filter;
E. Stirring and homogenising said particles received from step (D) with the diluent in the receiving chamber to obtain the pharmaceutical composition of the embodiments in the dry powder form; wherein said diluent is capable of colliding and continuous in-situ blending with the particles during the stirring in the receiving chamber, thereby preventing their aggregation and preserving their original size and shape; and
F. Additional mixing of the pharmaceutical composition obtained in (E) with an additional amount of the diluent to achieve the desired active agent-to-diluent ratio in said pharmaceutical composition.

In other embodiments, the clear and homogeneous solution of the active agent is obtained by dissolving the active agent either as a free base or as a salt in an organic solvent, a mixture of two or more organic solvents or in water. In particular embodiments, the pharmaceutical composition comprising the active agent may further comprise one or more pharmaceutically acceptable diluents, excipients or mixtures thereof. In some other embodiments, the pharmaceutical composition may be prepared in a form of a powder, simple powder mixtures, powder microspheres, coated powder microspheres, liposomal dispersions and combinations thereof.

Thus, the pharmaceutical composition of the embodiments may comprise at least one active agent and a diluent selected from the group consisting of lactose, lactose monohydrate, cellulose and derivatives, starch and derivatives, dextrose, sorbitol, mannitol, maltitol, xylitol or mixtures thereof. In some particular embodiments, the composition may be free of any other excipient than the diluent.

Active agents for intranasal inhalation in the dry powder form are usually produced by milling techniques. As a result, their particle size distribution is broad and their particle shapes are non-spherical and non-uniform. The active agent particles of less than 5 microns (μm) should however be avoided. They may reach the lungs mucosa by nasal spraying with a nasal spraying device or by inhaling with an inhalation device. This is completely unacceptable for intranasal administration from the safety point of view. Therefore, the production of the spherical-shape particles with the narrow particle size distribution larger than 5 μm and their use in nasal spraying and inhalation devices are beneficial for the intranasal administration. In yet further embodiments, the present application provides a process for obtaining dry powder particles of a spherical shape with a narrow particle size distribution by spray-drying a solution of at least one active agent free of diluent, and mixing the obtained dry powder particles of the at least one active agent with a diluent in the receiving chamber of the spray-drying apparatus under continuous stirring. In some embodiments, the pharmaceutical composition of the embodiments may be administered in an intranasal or oral solid dosage form.

Clear superiority of the intranasal composition of the present invention to the brain and plasma is shown in the in-vivo experiments.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

Disclosed embodiments will be understood and appreciated more fully from the following detailed description taken in conjunction with the appended figures.

DETAILED DESCRIPTION

Figure 1:
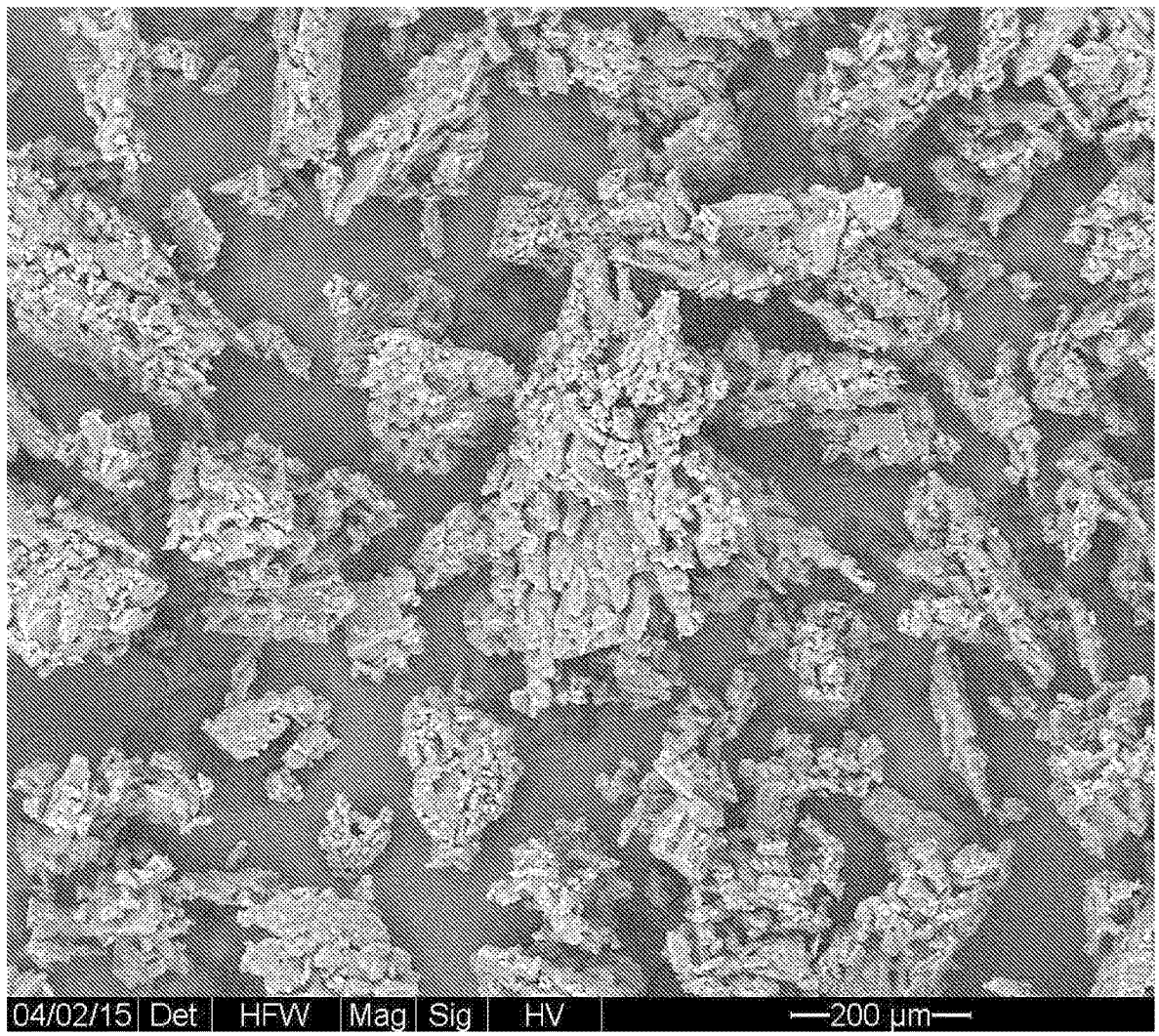
FIG. 1 shows the Scanning Electron Microscopy (SEM) image of sumatriptan succinate agglomerated powder, when the receiving chamber is empty (not prefilled with a diluent or disaggregation agent).

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The terminology used herein is for describing particular embodiments only and is not intended to be limiting of the invention. The term "comprising" and "comprises", used in the claims, should not be interpreted as being restricted to the components and steps listed thereafter; they do not exclude other components or steps. They need to be interpreted as specifying the presence of the stated features, integers, steps and/or components as referred to, but does not preclude the presence and/or addition of one or more other features, integers, steps or components, or groups thereof. Thus, the scope of the expression "a composition comprising A and B" should not be limited to compositions consisting only of components A and B. Also, the scope of the expression "a method comprising the steps X and Z" should not be limited to methods consisting exclusively of those steps.

Unless specifically stated, as used herein, the term "about" is understood as within a range of normal tolerance in the art, for example within two standard deviations of the mean. In one embodiment, the term "about" means within 10% of the reported numerical value of the number with which it is being used, preferably within 5% of the reported numerical value. For example, the term "about" can be immediately understood as within 10%, 9%, 8%, 7%, 6%, 5%, 4%, 3%, 2%, 1%, 0.5%, 0.1%, 0.05%, or 0.01% of the stated value. In other embodiments, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges, for example from 1-3, from 2-4, and from 3-5, as well as 1, 2, 3, 4, 5, or 6, individually. This same principle applies to ranges reciting only one numerical value as a minimum or a maximum. Unless otherwise clear from context, all numerical values provided herein are modified by the term "about". Other similar terms, such as "substantially", "generally", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value.

As used herein, the term "and/or" includes any combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The terms "active agent", "pharmaceutical active agent", "active", "API", "active pharmaceutical ingredient", "active substance", "active molecule", "active compound" or "drug" are used interchangeably.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealised or overly formal sense unless expressly so defined herein. Well-known functions or constructions may not be described in detail for brevity and/or clarity.

In one embodiment, a pharmaceutical composition in a form of dry powder for intranasal (nose-to-brain) N2B administration to a patient in need thereof comprises solid particles of at least one active agent and solid particles of a diluent, said pharmaceutical composition being substantially free of excipients other than the solid diluent, wherein said pharmaceutical composition having at least 90% of the particles of said at least one active agent with a mean particle size of 10-30 microns and less than 10% of the particles of said at least one active agent with a mean particle size equal to or below 5 microns. The particles of said diluent have a mean particle size of 30-200 microns.

The composition of the embodiment is essentially free of any excipients other than the solid diluent, such as lactose monohydrate or a lactose functional analogue. In another embodiment, a pharmaceutical composition in a form of dry powder for intranasal administration by transmucosal systemic delivery via the upper nose mucosa (the turbinate and lymphoid tissues located at the back of the nasal cavity) of a composition comprises an active agent having a mean particle size in the range of 10-30 microns, wherein at least 90% of its particles have a mean particles size of not less than 5 microns and not more than 30 microns. The particles of said diluent have a mean particle size in the range of 30-200 microns. As noted above, the diluent is also used for preventing aggregation of the dry powder particles containing at least one active agent.

At first sight, it would seem that the larger particle size might lead to a relatively lower N2B bioavailability of the active agent. However, this is offset by the better absorption of the larger particles of the active agent in the present invention, due to the longer residence time of the active on the nasal mucosa. Thus, a double advantage is obtained by administration of the dry powder composition of this specific particle size range: on one hand, better absorption of the active agent, and on the other hand, this mode of administration using delivery of relatively large particles directly to the upper region of the nasal cavity is substantially free of systemic effects due to lung delivery. In a further embodiment, the pharmaceutical composition for intranasal N2B administration comprises an active agent having a particle size in the range from about 10 microns to about 30 microns, and more than 90% particles of the active agent are above 5 microns, and wherein the active agent is delivered to the superior region of the nasal cavity. In yet further embodiment, the composition comprises an active agent having a mean particle size range of 10-30 microns, wherein at least 90% of its particles have a mean particles size of not less than 5 microns and not more than 30 microns, and a diluent with a particle size in the range of 30-200 microns, said composition may be administered either by nose-to-brain (N2B) delivery or by systemic delivery, or both.

In some embodiment, the intranasal delivery method of the present application provides delivery of dry powders to the nasal mucosa, olfactory region, the trigeminal nerve and other structures of the limbic system. In another embodiment, the pharmaceutical composition is used to deliver the active agent to the upper region of the nasal cavities. This upper region represents the only region where it is possible to circumvent the blood-to-brain barrier and enable transport to the cerebrospinal fluid (CSF) and the brain.

The composition of the embodiments may be delivered by any one of the known in the art nasal devices, such as pressurised devices, dry powder sprayers or bi-directional nasal devices. Multi-dose devices as well as single-dose devices may be used.

In some embodiments, the desired attributes for an intranasal powder formulation with commercial potential required in EMA and FDA Guidelines[8] are inherent features of the compositions of the embodiments. The uniform dose deliverability of the initial and stored formulation by a device for intranasal administration is exemplified in Example 22. None of the dose measurements was found to be outside 75-125% of the label claim.

[8] EMA Guideline: Guideline on the Pharmaceutical Quality of Inhalation and Nasal Products (June 2006); FDA Guidance for Industry (Chemistry, Manufacturing & Controls Documentation): Metered-Dose Inhaler (MDI) & Dry Powder Inhaler (DPI) Drug Products (October 1998).

Figure 2:
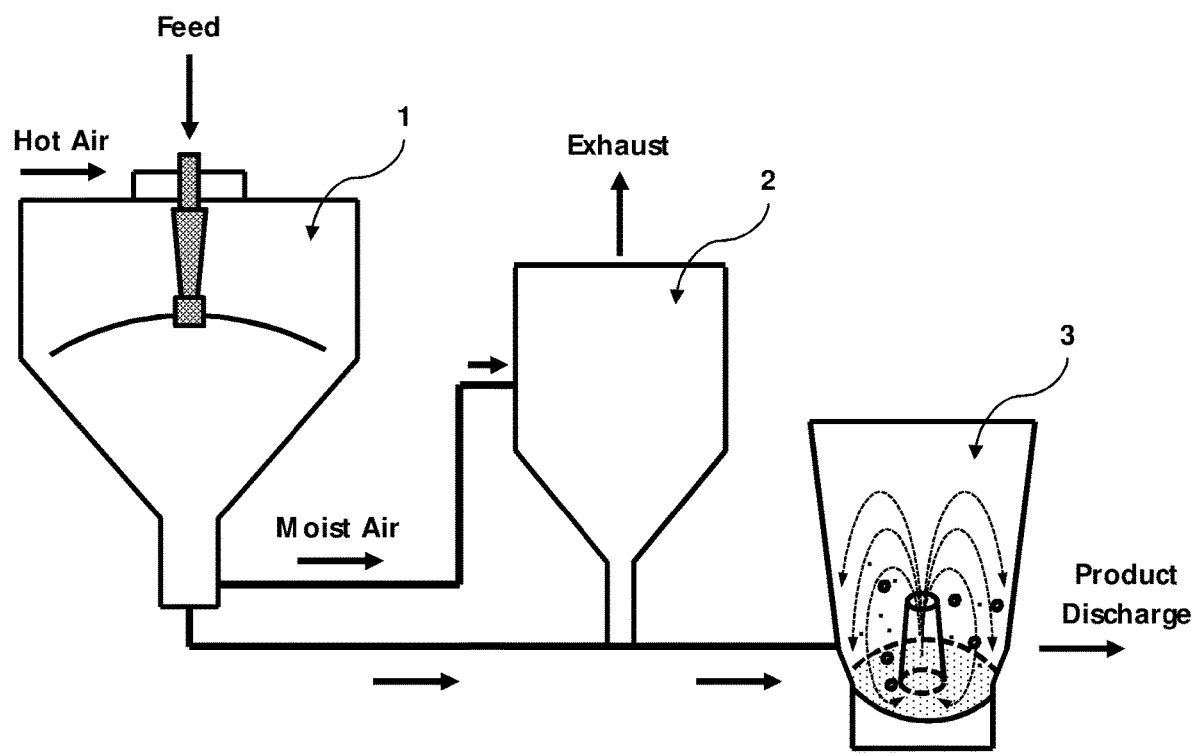
FIG. 2 shows the schematic drawing of the modified spray-dryer apparatus of the embodiments, suitable for the particles engineering and prevention of agglomeration.

The present application provides an apparatus and a method for the manufacture of a pharmaceutical composition in a form of dry powder for intranasal delivery having less than 5% of small particles below 5 microns, to exclude undesirable administration to the lungs. FIG. 2 schematically shows the apparatus for the preparation of the pharmaceutical composition of the embodiments in a dry powder form, said apparatus comprises the following components:

a) A spray-drying chamber [1] capable of spray-drying a clear and homogeneous solution of at least one active agent to obtain dry powder particles of said at least one active agent in a moist air, said solution being free of diluent;
b) A cyclone separator [2] capable of receiving said dry powder particles and the moist air stream from said spray-drying chamber [1], separating said particles from the moist air through vortex separation, exhausting the air and transferring the separated particles to a receiving chamber [3] through a bag filter; and
c) The receiving chamber [3] (or "receiver") pre-filled with a diluent and adapted for receiving the separated dry powder particles from the cyclone separator [2], mechanically stirring and homogenising said particles with the diluent to obtain the pharmaceutical composition in the dry powder form of the embodiments; wherein said diluent is capable of colliding and continuous in-situ blending with the particles during the stirring in the receiving chamber [3], thereby preventing their aggregation and preserving their original size and shape.

The spray-drying chamber is equipped with nozzles, which are used to produce droplets of the active agent solution, to control the droplet and powder particle size and to maximise heat transfer and the rate of solvent vaporisation. The spray-dryer apparatus of the embodiments thus receives a stream of the liquid solution containing the active agent, sprays it through the nozzles into a hot gas stream, such as nitrogen or air, and removes the solvent as a vapor. As the moisture quickly leaves the droplets, the dry powder is produced. The droplet size may range from 20 to 180 μm, depending on a particular nozzle used. In the present embodiments, the sprayed solution of the active agent is free of any diluent.

The nozzles are designed to spray the solution of the active agent into a hot air flow, thereby achieving a thorough mixing and uniform distribution of the hot air flow and sprayed solution in the spray-drying chamber to produce a substantially complete evaporation of liquids and drying of solid particles of the active agent from the mixture throughout said chamber. In a specific embodiment, the spray-drying chamber is equipped with a two-fluid nozzle having an appropriate opening controlling the API particles size in the range of 10-30 μm. One of the fluids is an active agent solution, free of any diluent, and the other fluid is a drying gas or air.

At the laboratory scale, the stirring and homogenisation is achieved by using a magnetic stirrer and a magnetic bar of appropriate size, in addition to the rotation of the receiving chamber. At industrial scale, the stirring and homogenisation may be achieved by using a mechanical stirrer of appropriate size and form, or moving, rotation and vibration of the whole receiving chamber. A conventional spray-drying apparatus contains the empty receiving chamber collecting the dry powder particles of an active agent. This receiver is emptied from time to time in order to ensure the continuous process. In contrast, the present application discloses the receiving chamber pre-filled with a continuously stirred diluent for preventing aggregation of the dry powder particles and preserving their original size and shape.

The method for the preparation of the pharmaceutical composition of the embodiments in a dry powder form is based on the spray-drying process rapidly drying the solution of at least one active agent, free of any diluent or excipient, with hot air, thereby producing a dry powder of the active agent. This method comprises the following steps:

A. Preparing a clear and homogeneous solution of at least one active agent in an organic solvent or solvent mixture, in a solvent-water or water miscible solvent mixture, or in water.
B. Filling the receiving chamber with a diluent and continuously stirring the diluent in the receiving chamber;
C. Streaming the solution prepared in step (A) together with hot gas to the spray-draying chamber, spray-drying the solution in the spray-drying chamber to obtain dry powder particles of said at least one active agent in a moist gas, and transferring the obtained dry powder particles and the moist gas stream to the cyclone separator;
D. Separating said particles from the moist gas through vortex separation in the cyclone separator, exhausting the gas and transferring the separated particles to the receiving chamber through a bag filter;
E. Stirring and homogenising said particles received from step (D) with the diluent in the receiving chamber to obtain the pharmaceutical composition of the embodiments in the dry powder form; wherein said diluent is capable of colliding and continuous in-situ blending with the particles during the stirring in the receiving chamber, thereby preventing their aggregation and preserving their original size and shape; and
F. Adding diluent and additionally mixing of the pharmaceutical composition obtained in step (E) with the additional amount of the diluent to achieve the desired active agent-to-diluent ratio in said pharmaceutical composition.

The gas used in the spray-drying process is normally air. However, if the solvent is flammable, for example ethanol, or the product is oxygen-sensitive, then nitrogen or any other suitable inert gas may be used instead.

In a particular embodiment, the clear and homogeneous solution of the active agent is obtained by dissolving an active agent either as a free base or as a salt in an organic solvent, a mixture of two or more organic solvents or in water. The gas outlet temperature in the method of the embodiments is generally about 75° C. or below, preferably about 70° C. or below, more preferably about 59° C. or below, yet more preferably about 52° C. or below, or about 50° C. The gas inlet temperature is generally about 75° C. or higher, preferably about 80° C. or higher, more preferably about 90° C. or higher, yet more preferably about 100° C. or higher, even more preferably about 110° C. or higher, or about 120° C. The volatile products obtained in the process are the organic solvents and/or water. The volume of water should be 50% or more of the volume of the volatiles. In the specific embodiment, a Class 3 organic solvent is used in the method for the preparation of the pharmaceutical composition in a dry powder form. The residual solvent content after drying is less than 0.5%.

The drug (active agent) content of the composition of the embodiments may be adjusted so as to provide the total dose of the drug required to achieve the therapeutic effect as a single dose in a single nostril. The drug administration can be repeated in the second nostril in order to double the amount of the active material. Stability of the composition of the embodiments on storage was determined under accelerated and ambient conditions.

The device used for the intranasal delivery of the compositions of the embodiments may be engineered so as to provide the appropriate plume geometry and spray pattern of initial and stored compositions. In some embodiments, these compositions may have a narrow particle size distribution with median diameter between 10 to 20 microns.

Figure 8A:
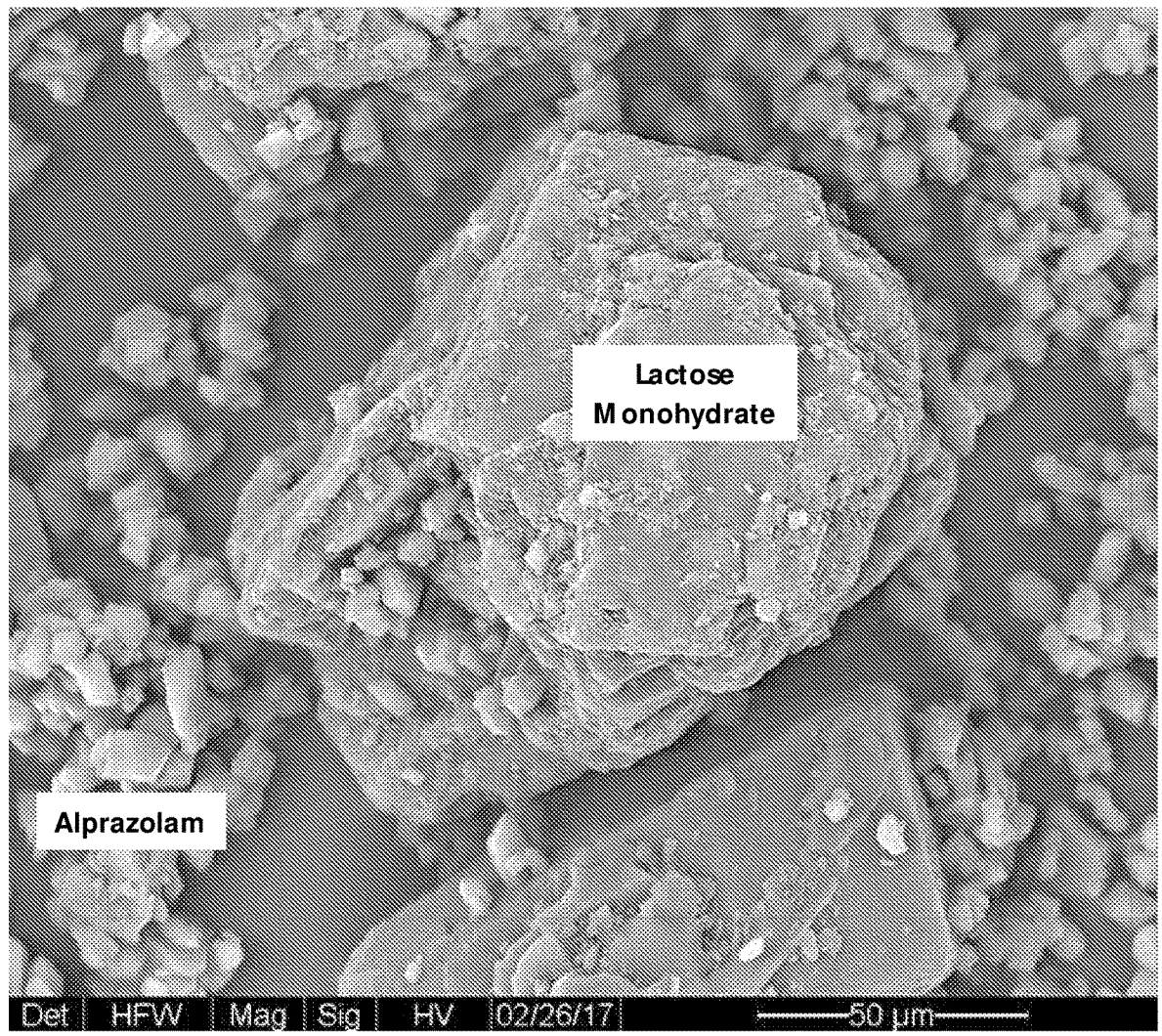
FIG. 8a shows the SEM image (X1200) of lactose monohydrate (large polyhedrons) and alprazolam (small polyhedrons) of the dry powder composition of the embodiments for nasal administration formulation.
Figure 8B:
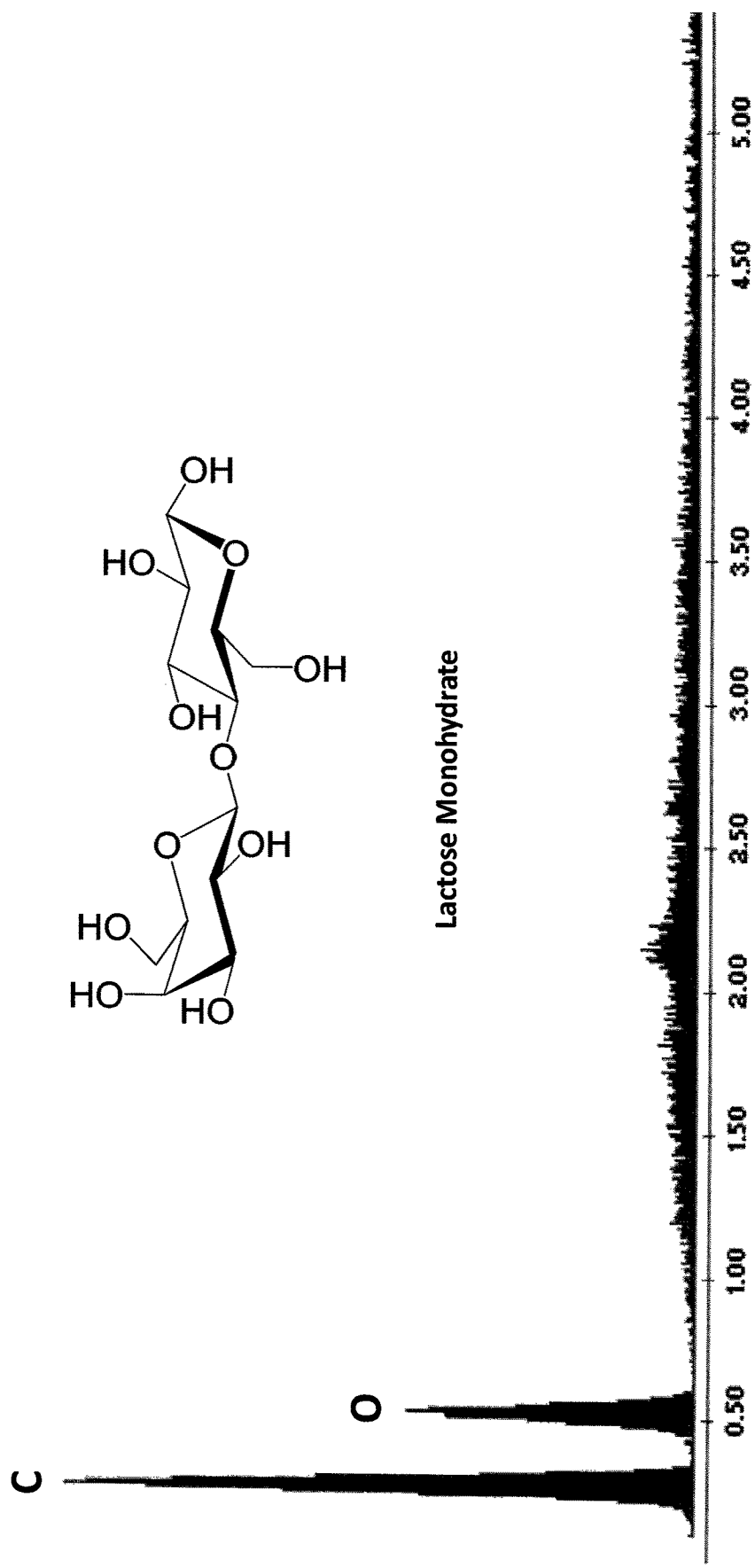
FIG. 8b shows the X-ray elemental analysis of the large polyhedrons confirming that these are the particles of lactose monohydrate containing "C" and "O" atoms.
Figure 8C:
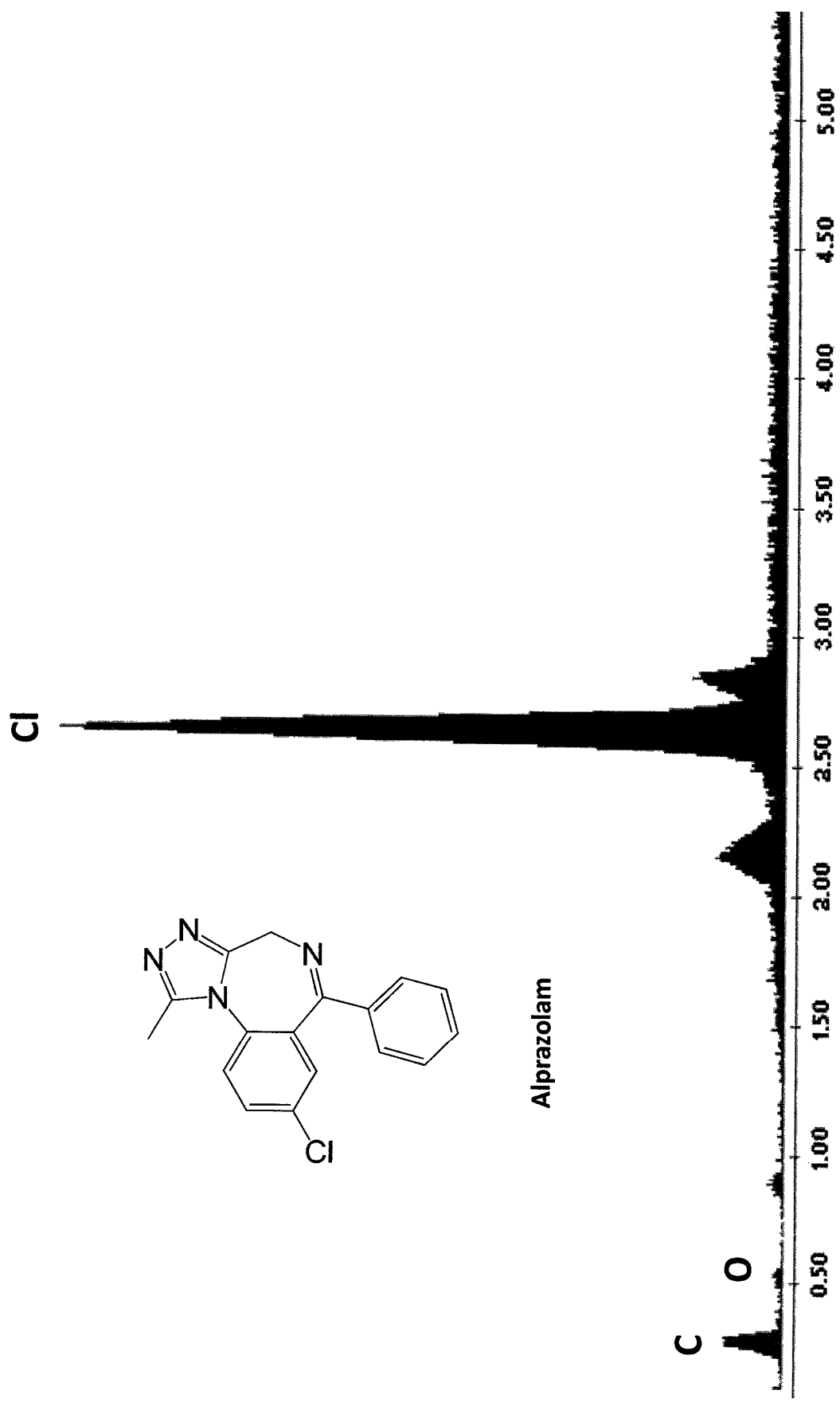
FIG. 8c shows the X-ray elemental analysis of the small polyhedrons confirming that these are the particles of alprazolam containing "C", "O" and "Cl" atoms.

The shape and particle morphology of the dry powder of the embodiments for intranasal delivery were characterized using an electron microscope. Reference is now made to FIGS. 8a-8c and Example 13 (in the experimental section below) showing the polyhedron shape of the particles. FIGS. 3, 4, 9 and 11 show spherical particles, contribution of which may be more significant in reaching the deeper region of the nasal passage.

The process of the embodiments for the preparation of the pharmaceutical composition of the present embodiments in a dry powder form for nasal delivery produces preponderantly a spherical population of particles. In rare cases, the active agent may form a polyhedron-shape crystalline particles or spherical/polyhedron mixtures.

Many previous attempts at developing an intranasal powder formulation fell short in one or several of the desired properties including satisfactory safety and tolerability profile. The compositions of the embodiments are designed to have some or all of these desired properties. These compositions have two required components:

(a) The active agent may be hydrophilic or lipophilic active agent, wherein the hydrophilic active ingredient may be delivered via olfactory mucosa to the brain and the lipophilic active agent may be delivered via nasal mucosa to systemic circulation and then to the brain, by-passing the liver.

(b) Lactose monohydrate or a lactose monohydrate functional analogue also used for preventing aggregation of the active agent particles and preserving their original size and shape.

The active agent of the embodiments is a hydrophilic or lipophilic, chemical or biochemical, solid therapeutic substance selected from compounds for use in common cold treatment, anti-addiction agents, anti-infective agents, analgesics, anaesthetics, anorexics, antarthritics, anti-allergy agents, antiasthmatic agents, anticonvulsants, anti-depressants, antidiabetic agents, anti-depressants, anti-diuretics, anti-emetics, antihistamines, anti-hypertensive agents, anti-inflammatory agents, antimigraine preparations, anti-motion sickness preparations, antinauseants, antineoplastics, anti-obesity, antiosteoporosis, anti-Parkinsonism drugs, antipruritics, antipsychotics, antipyretics, anticholinergics, benzodiazepine antagonists, bone stimulating agents, central nervous system stimulants, hormones, hypnotics, immunosuppressives, prostaglandins, proteins, peptides, polypeptides and other macromolecules, psychostimulants, compounds for use in rhinitis treatment, compounds for use in sexual hypofunction treatment, sedatives, compounds for use in treatment of known or suspected opioid overdose, tranquilizers and vitamins, probiotics, natural ingredients, peptide or protein therapeutic agents such as cytokines, hormones, clotting factors, vaccines, monoclonal antibodies, amino acids, or any combination thereof.

In some embodiments, the active agent is selected from sumatriptan succinate, zolmitriptan salts, naratriptan, rizatriptan, almotriptan, eletriptan, frovatriptan, bupivacaine, fibroblast growth factor, cephalexin, lidocaine, clobazame, midazolam, alprazolam, diazepine, lorazepam, dexmedetomidine, monosialoganglioside, cocaine, insulin, glucagon, oxytocin, fentanyl, sulfentanil, diamorphine, ketamine, apomorphine, buprenorphine, morphine sulphate, oxycodone hydrochloride, butorphanol, NSAIDs, paracetamol, benzodiazepines, dopamine, pramipexole, rasagiline, rogitine, ondansetron, granisetron, metoclopramide, naloxone, naltrexone, atropine, adrenaline, cannabis active compounds, epinephrine, isosorbide dinitrate, obitoxine, dexmedetomidine, metochlorpramide, L-dopa, nicotine, sildenafil, nafarelin, dobutamine, phenylephrine, tramazoline, xylometazoline, tramadol, methacholine, ipratropium, scopolamine, propranolol, verapamil, hydralazine, nitroglycerin, clofilium tosylatecannabis active compounds and pharmaceutically acceptable salts, isomers, and mixtures thereof.

In a specific embodiment, the dry powder of the active agent for nasal delivery contains at least 90% of the particles having a mean particle size of 10-30 microns, and less than 10% of the particles having a mean particle size equal to or below 5 microns. The particle size is measured using the laser diffraction method. The active agent particles may have spherical, ellipsoid, polyhedron, cubic, plate, or needle shapes. The preferable particle shapes are spherical and ellipsoid. These shapes provide the best aerodynamic properties of the active agents. The drug particle shape and morphology is determined using the electron microscopy.

The solid diluent of the embodiments is selected from lactose monohydrate or a lactose monohydrate functional analogue, such as lactose, cellulose and derivatives, starch and derivatives, dextrose, sorbitol, mannitol, maltitol, xylitol or mixtures thereof. The preferred solid diluent is lactose monohydrate.

Lactose may be present in the form of α-lactose monohydrate, anhydrous β-lactose or amorphous lactose. α-Lactose monohydrate is a commonly used DPI (dry powder inhaler) excipient, and is a pharmacopeia excipient for DPIs in a pulmonary delivery route. Lactose monohydrate of the embodiments has a bulk density of 0.6-0.8 g/ml and partly tomahawk-shaped crystals with the following particle size distribution: $D_{10}$ 30-60 µm; $D_{50}$ 70-110 µm and $D_{90}$ 110-150 µm.

According to Jagdeep Shur et al, "*From single excipients to dual excipient platform in dry powder inhaler products*", International Journal of Pharmaceutics (2016), 514, pages 374-383, the single excipient platform (SEP) has been the most prevalent excipient strategy used in many commercial DPI products. The majority of approved SEP DPI products have been developed based on the well-known 'carrier' approach. The role, or functionality, of the single excipient in the SEP-based DPI products has traditionally been described as a 'dispersant', 'filler', 'diluent' or 'carrier'. The 'carrier' description is now so commonplace in academic, industrial and regulatory circles that in 2014 it was incorporated into the updated respiratory section of the United States Pharmacopoeia (General chapter 1059). Such 'carrier' excipients, often of a small particle size, are also used in what are described as 'agglomerate' formulations. This is in contrast to the large particle size (50-200 microns) of lactose or lactose functional analogue of the embodiments. Thus, unlike the regular DPIs, the excipient of the embodiments (such as lactose or lactose functional analogue) has rather large particle size (50-200 microns), and—while being multi-functional, it is mainly used as a diluent and carrier for preventing agglomeration of much smaller particles of an active agent, deagglomeration of the particles and homogenisation of the composition. Therefore, the excipient of the embodiments is referred to throughout the present application as "diluent".

It is a surprising and unexpected finding that the lactose monohydrate solid diluent of the embodiments may serve for preventing aggregation or agglomeration of the active agent particles, or as a disaggregant or de-agglomerating agent in the preparation of the dry powder composition for intranasal administration, when the spray-dried active agent and the diluent are mixed in-situ in the receiving chamber of the spray-drying apparatus. It is indeed unpredictable and surprising that the large particles of lactose monohydrate with a mean diameter of 50-200 µm are capable of preventing the aggregation of the small active agent particles with a mean diameter of 10-30 µm. The lactose monohydrate particles cannot therefore enter the nasal passage and become swallowed after actuation.

Thus, the compositions of the embodiments comprise at least one active agent and a diluent, such as lactose or a lactose functional analogue, and are substantially free of other excipients, such as surfactants, lipid agents, solvents or propellants. Most of the DPI formulations rely on lactose monohydrate as a diluent. However, lactose cannot be used in the compositions comprising active compounds that interact with the reducing sugar function of lactose in the Maillard reaction. Lactose functional analogues of the embodiments, which may be used as a solid diluent instead of lactose and may replace lactose in some compositions, particularly as an alternative for patients suffering from lactose intolerance, are selected from cellulose and derivatives, starch and derivatives, mannitol, glucose, sorbitol, maltitol, xylitol or mixtures thereof. The particle size of these diluents is also in the 50-200 µm range.

The pharmaceutical composition of the embodiments may further comprise one or more pharmaceutically acceptable diluents, excipients or both. The pharmaceutical composition of the embodiments may be prepared in the form of a powder, simple powder mixtures, powder microspheres, coated powder microspheres, liposomal dispersions or combinations thereof.

The conventional spray drying process uses an empty receiving chamber in the beginning of the process. Such receiving chamber is filled with the spray-dried product powder and emptied from time to time in order to ensure the continuous process. In the present embodiments, the receiving chamber is however pre-filled with the continuously stirred diluent for preventing agglomeration or de-agglomeration of the active agent particles. The regular methods for the preparation of dry powders for nasal delivery usually use surfactants and lipid agents for disaggregation and de-agglomeration of the solid particles and for preventing their aggregation. It was surprisingly and unexpectedly found that rather coarse particles of the diluent, such as lactose or lactose functional analogue, with the size range of 50-100 µm prevent aggregation of the active agent particles having the size range of 10-30 µm. In a further embodiment, a method for disaggregation and de-agglomeration of the active agent dry powder and for preventing its solid particles aggregation comprises in-situ mechanical mixing of the agent dry powder with a diluent, preferably lactose monohydrate, in the receiving chamber of the spray-drying apparatus of the embodiments.

The active agent for nasal inhalation in a dry powder form is usually produced by jet or wet milling techniques that give rise to broad particle size distribution and to non-spherical and non-uniform shapes of the particles. In addition, the jet or wet milling methods produce particles of less than 5 µm. These coarse inhalable particles of less than 5 µm may easily reach the lungs by nasal spraying (with a nasal spraying device) or by inhaling (with an inhalation device) and cause tiny wounds and scarring to the lungs: each time this happens, it causes a very small amount of irreversible damage. The immediate effect is unnoticeable, but over some periods of time, this can result in significantly decreased lung capacity, and a number of other health issues. Therefore, production of the dry powder particles ranging from 2-10 µm, particularly less than 5 µm, for the intranasal administration should be avoided by all means. The present application provides solution also to this problem by disclosing the method for the preparation of the active agent particles of the embodiments having a spherical shape with a narrow size distribution (10-30 µm), which are safe for use in nasal spraying or inhaler devices.

In some embodiments, there is provided a mode of administration of an active agent by nasal delivery, wherein the active agent has a particle size more than 10 µm and a narrow size distribution range, the particles are substantially spherical or ellipsoid and the composition comprising this active agent is administered by a spraying with a nasal spraying device or inhaling with an inhaler device.

As described above, the preparation method of the embodiments is characterised by the two major steps: the drying, more preferably spray-drying, of the active agent clear and homogeneous solution, and then mixing the obtained dry powder with the solid diluent, such as lactose or lactose functional analogue, thereby obtaining the composition of the embodiments in a form of dry powder consisting of an active agent and a solid diluent, said composition having a particle size ranging from 10 to 30 µm and a spherical shape of the drug particle. This is in contrast to spray-drying processes described in the patent documents U.S. Pat. No. 6,462,090, US 20080292713, US 20150010633 and US 20160354288, which yield the composite active agent particles with the particle size less than 5 µm. The spray-drying step in the process of the embodiments yields active agent particles larger than 10 µm. These particles are then in-situ blended with the solid diluent, such as lactose, to prevent the growth of the particles and their agglomeration.

The compositions of the embodiments for intranasal administration containing the active compounds, such as analgesics, opioids or triptans may be used for the fast and efficient pain relief.

To sum up, in some embodiments, there is provided a pharmaceutical composition, wherein the solid diluent is the only excipient, said solid diluent is used for prevention of active agent aggregation in said composition. In some embodiments, there is provided a pharmaceutical composition, wherein the dry powder particles of the active agent are substantially in a spherical form. In some embodiments, a therapeutically effective dose of the pharmaceutical composition of the embodiments may be intranasally administered to a patient in need thereof, wherein the administration is targeted at the uppermost region of the nasal cavity, thereby resulting in the nose-to-brain (N2B) delivery of the active agent to the brain of the patient, or in the transmucosal systemic administration. In some embodiments, there is provided a method of treatment, wherein the administration delivers an entire therapeutically effective dose of at least one active agent to one nostril. In some embodiments, there is provided a method of treatment, wherein the therapeutically effective dose of at least one active agent is administered once daily. In some embodiments, there is provided a method of treatment, wherein the therapeutically effective dose of at least one active agent is lower than the therapeutically effective dose of a similar intranasal composition using a non-N2B mode of delivery.

Figure 14:
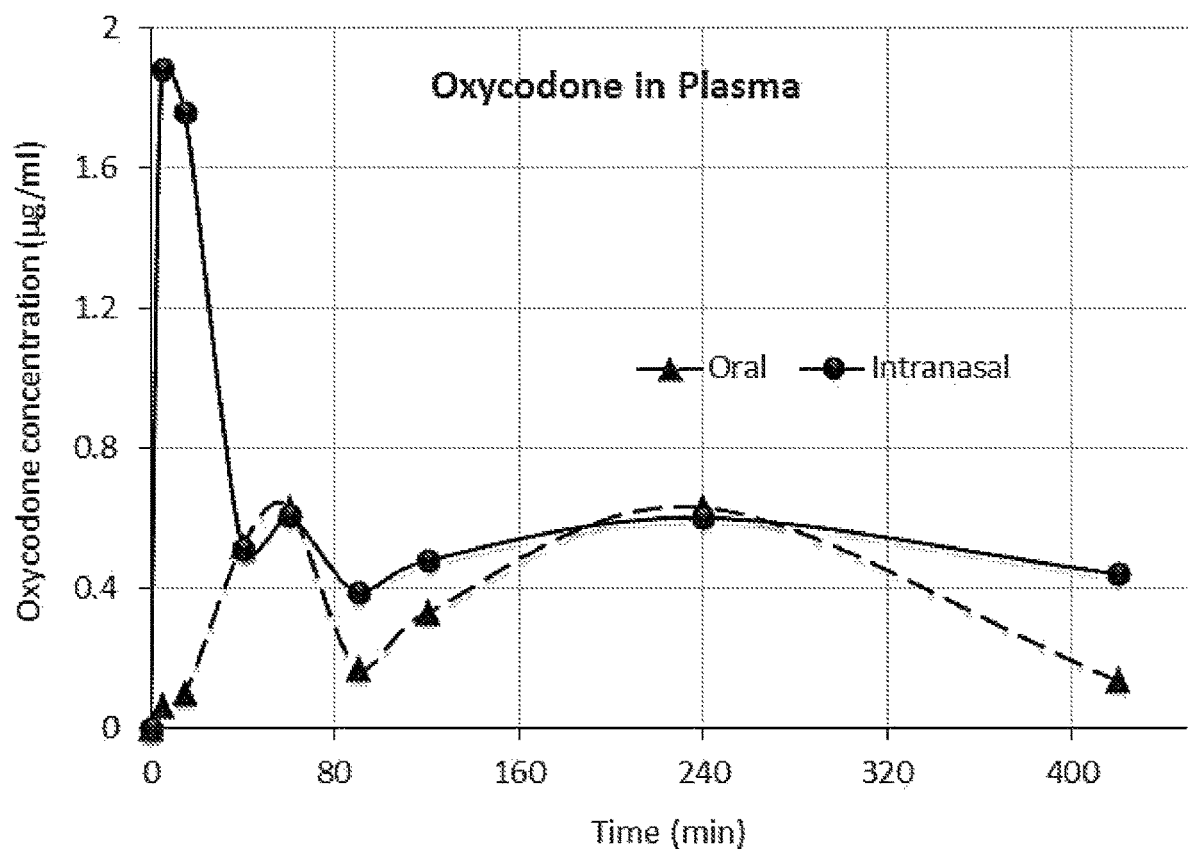
FIG. 14 shows the oxycodone pharmacokinetic profiles in rat's plasma following administration of oral gavage (oral) and intranasal powder (intranasal) to 12 SD rats at dose of 10 mg/kg.
Figure 15:
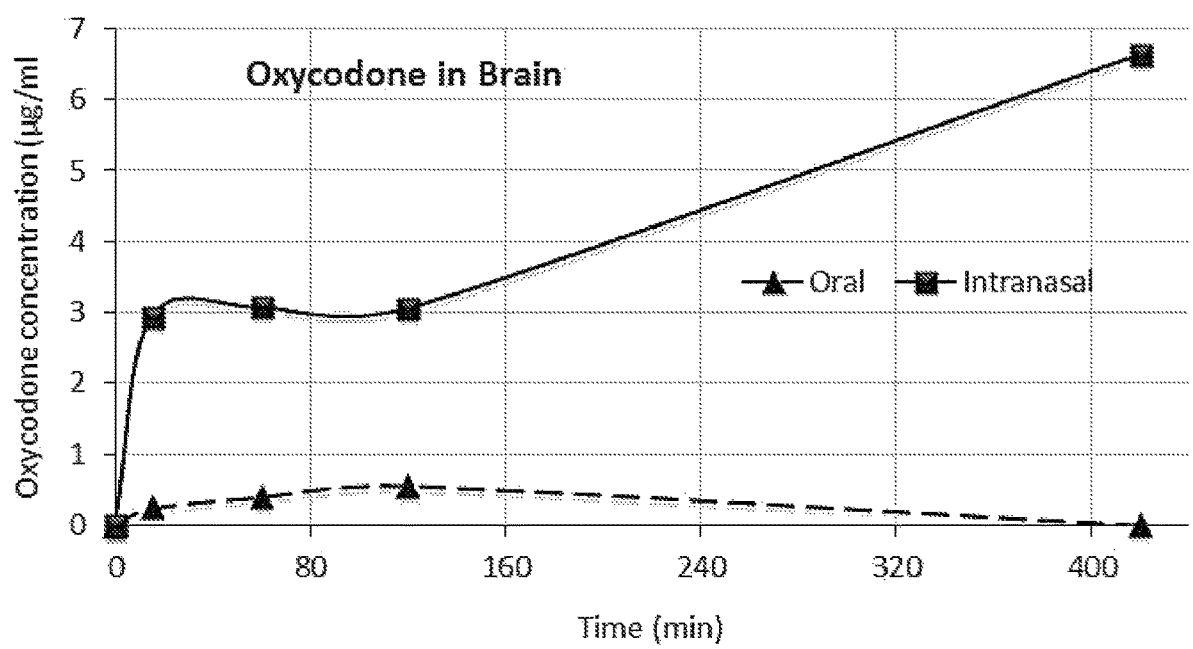
FIG. 15 shows the oxycodone pharmacokinetic profiles in rat's brains following administration of oral gavage (oral) and intranasal powder (intranasal) to 12 SD rats at dose of 10 mg/kg.

The significantly improved pharmacokinetic profile and superior effects of the intranasal composition of the present invention on the brain and plasma compared to the oral solution are shown in the in-vivo experiments (see Example 24, and FIGS. 14-15). The faster onset of action and higher drug concentration in plasma were demonstrated for the intranasal powdered composition of the present invention compared to the oral solution. In addition, the faster onset of action and higher sustained drug concentration in brain was demonstrated for the intranasal powdered composition of the present invention compared to the oral solution.

EXAMPLES

The following examples illustrate certain features of the present invention but are not intended to limit the scope of the present invention. In the examples below, the term "ratio" refers to the weight/weight ratio, except the cases where use of other units is specifically referred to in the text.

Materials

Sumatriptan succinate (from SMS); lactose monohydrate (from Meggle Pharma); morphine sulphate and oxycodone hydrochloride (from Noramco); naloxone hydrochloride (from Cilag); acetaminophen (from Greenville Plant); cannabidiol (from THC Pharm); alprazolam (from Centaur); dopamine hydrochloride and insulin (from Sigma-Aldrich); pramipexole dihydrochloride (from LGM Pharma); ondansetron hydrochloride (from Teva), ethanol and acetone (from BioLab).

Methods

The spray-drying process was carried out using the Mini Spray Dryer B-290 of Büchi Labortechnik AG. A magnetic stirrer (Fried Electric) was placed under the receiver (receiving chamber), a magnetic bar of appropriate size was inserted into the receiver, and then the diluent was added. The liquid feed containing at least one active agent was prepared by dissolving at least one active compound in the selected solvent or mixture of solvents. Quantification was performed using HPLC and a Dionex HPLC instrument. A FEI Quanta-200 Scanning Electron Microscope (SEM) equipped with an Everhart-Thornley Detector was used to obtain the images of the spray-dried powder. The accelerating voltage of 20 kV was applied to provide magnification from 250 to 10,000 times. In addition, an X-ray Element Analysis Detector (Link ISIS, Oxford Instruments, GB) was used to determine the drug and particle identity and their distribution throughout DPI. Particle size was measured using the Malvern Mastersizer 3000 series based on the Light Diffraction method.

Oxycodone assay in the compositions was performed using Dionex HPLC-PDA instrument equipped with Chromeleon software. Column: Agilent, ZORBAX SB-CN 4.6×250 mm, 5 μ. Mobile phase: 50 mM potassium dihydrogen phosphate buffer (pH 3.0): acetonitrile (40:60%, v/v). Flow rate: 1.0 mL/min. Column temperature: 25° C. Injection volume: 10 μL.

Oxycodone bio-assay in rat's plasma and brains' oxycodone assay in the compositions was performed using Dionex HPLC-PDA instrument equipped with Chromeleon software. Detector: UV at 210 nm. RT of oxycodone: about 2.6 min. Diluent: water standard and sample final concentration about 4 μg/mL. Column: Agilent, ZORBAX SB-CN 4.6× 250 mm, 5 μ. Gradient: mobile phase A: 50 mM potassium dihydrogen phosphate buffer (pH 3.0): acetonitrile (45:10%, v/v); mobile phase B: acetonitrile. Flow rate: 1.0 mL/min Column temperature: 25° C. Injection volume: 50 μL. Detection: UV at 210 nm. PDA 200-400 nm. Calibration curve: from 0.1 μg/mL to 4 μg/mL prepared by spiking with rat plasma. Quantitative limit: 0.05 μg/mL. Internal standard: alprazolam.

Processing Oxycodone HCl in Rat Plasma

100 μl plasma (serum) spiked with IS mixed with 600 μL of acetonitrile for precipitation protein and centrifuged at 14000 rpm for 10 min. Supernatant was dried under nitrogen and reconstituted with 100 μL potassium dihydrogen phosphate buffer (pH 3.0).

Processing Oxycodone HCl in Rat Brain

Each individual brain tissue was previously weighted and treated by 0.1M perchloric acid and homogenized. Then it was spiked with IS and mixed with 1400 μL of acetonitrile. After centrifugation at 14000 rpm for 10 min, the upper layer was centrifuged again. Supernatant was dried under nitrogen at 40° C. and reconstituted with 100 μL potassium dihydrogen phosphate buffer (pH 3.0).

Example 1

Spray-Drying of Sumatriptan Succinate Solution Without Lactose

This is the reference example for the comparison purposes only. Sumatriptan succinate (12.0 g) was dissolved in 100 ml of deionized (DI) water under stirring at 300 rpm. The resultant clear homogeneous solution was spray-dried using a Büchi Mini Spray-Dryer with inlet air temperature of 105° C. and outlet temperature of 62° C., thereby obtaining the dry powder. SEM image (see FIG. 1) showed that the obtained powder was highly aggregated. Large aggregates up to 500 microns (μm) are clearly seen on the image.

Example 2

Modification of the Commercial BüChi Labortechnik AG Spray-Dryer

FIG. 2 schematically shows a modified spray dryer of the embodiments. A Mini Spray-Dryer B-290 of Büchi Labortechnik AG was modified by:
1. Addition of a magnetic bar into the glass receiver and placing a magnetic stirrer under the continuously rotating glass receiver of the spray-dryer.
2. Selection of a suitable two-fluids spraying nozzle for spraying the solution containing only an active agent (without diluent) into fine droplets suitable for the preparation of 10-30 μm dry powder particles of the active agent. One of the fluids is the clear and homogeneous solution of the active agent, and the second fluid is the drying gas.

Example 3

Sumatriptan Succinate Composition with Lactose Monohydrate

Sumatriptan succinate (2.3 g) was dissolved in a mixture of acetone (12 g) and ethanol (12 g) under stirring at 300 rpm. An appropriate size magnetic bar was placed in the receiver and lactose monohydrate (2.3 g) was added there. The stirring rate was set at 150 rpm. The clear and homogeneous solution of the active agent (sumatriptan succinate) was spray-dried using the Büchi Mini Spray-Dryer with inlet air temperature of 60° C. and outlet temperature of 55° C., thereby obtaining the dry powder of the active agent, which was further blended with lactose monohydrate in-situ in the receiver. Stirring was being maintained during the entire process. The actual weight of sumatriptan as an active agent in the obtained sumatriptan/lactose composition was 15.4%. The composition was then mixed with an additional amount of lactose in order to reach the required 10% active agent (sumatriptan) concentration.

Example 4

SEM Imaging of the Sumatriptan Succinate Composition

Figure 3:
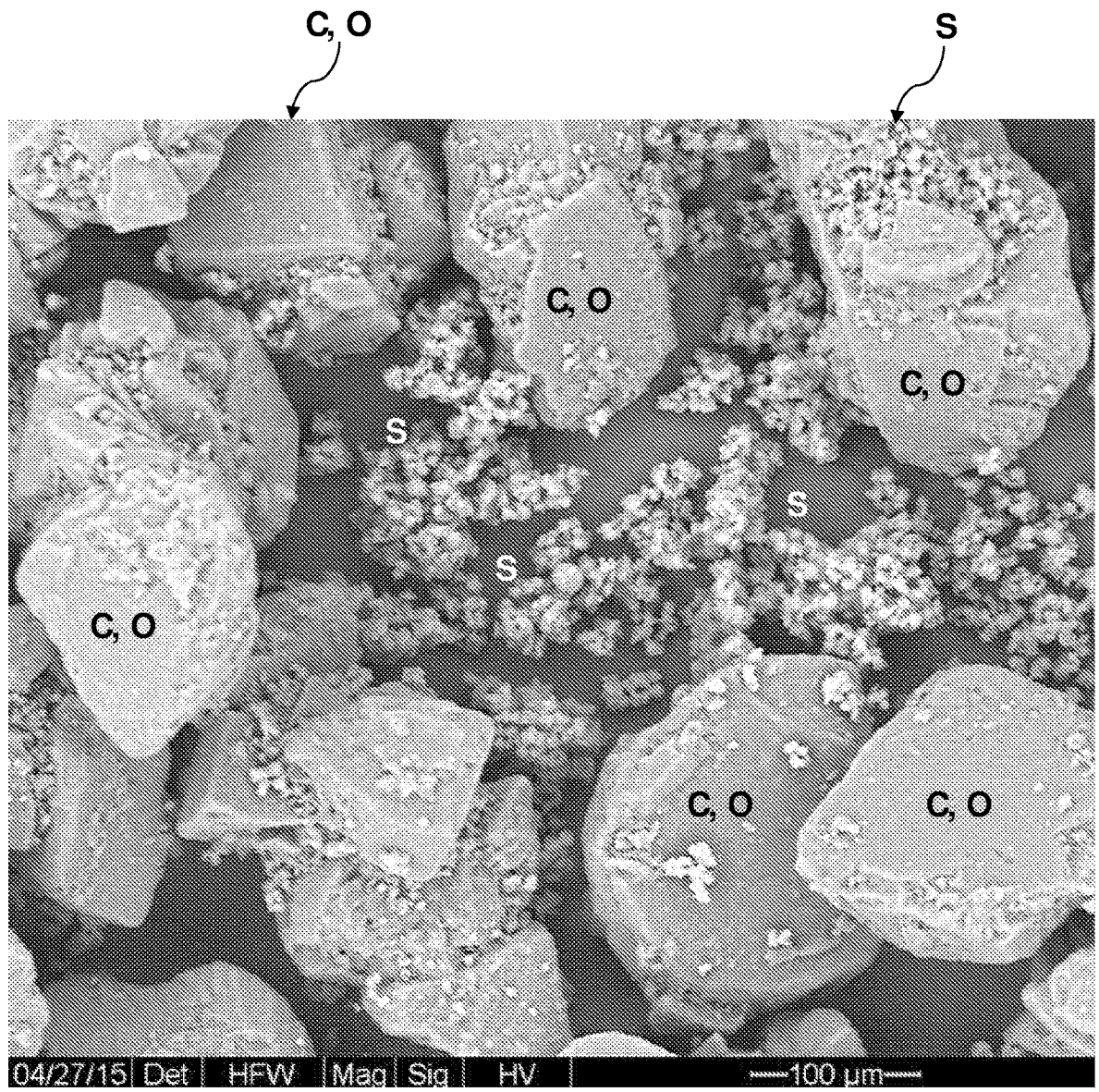
FIGS. 3 and 4 show the SEM images of lactose monohydrate (large cubic particles or tomohawks comprising "C" and "O" elements) and sumatriptan succinate particles (small spherical particles comprising also "S" element) of dry powder for intranasal delivery formulation.
Figure 4:
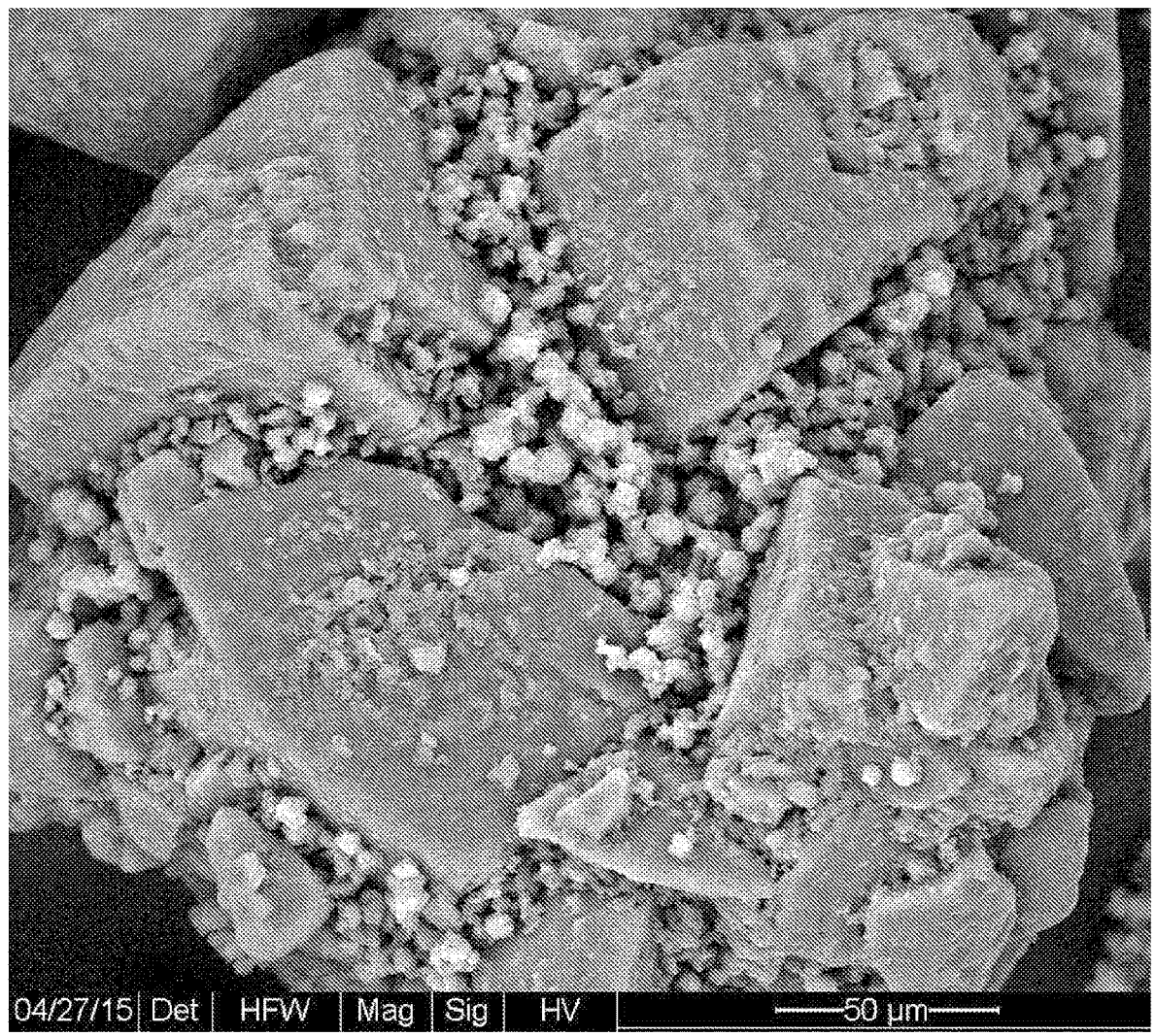

High resolution SEM imaging coupled with an X-ray Element Analysis Detector provides the unique opportunity to identify each individual particle of a formulation by its chemical content. Using this technique, the particles of sumatriptan succinate containing sulphur (S) atoms can be differentiated from lactose particles containing carbon (C) and oxygen (O) atoms (without sulphur). FIGS. 3 and 4 show the small spherical API particles having a narrow size distribution ranging from 5 µm to 20 µm, which are dispersed between large lactose polyhedron particles of ranging from 50 µm to 200 µm. FIG. 3 shows the high-resolution image with the 100-µm bar and the elemental analysis of the particles. FIG. 4 shows the high-resolution image with the 50-µm bar.

Example 5

Particle Size Analysis of the Sumatriptan Succinate Composition

Figure 5:
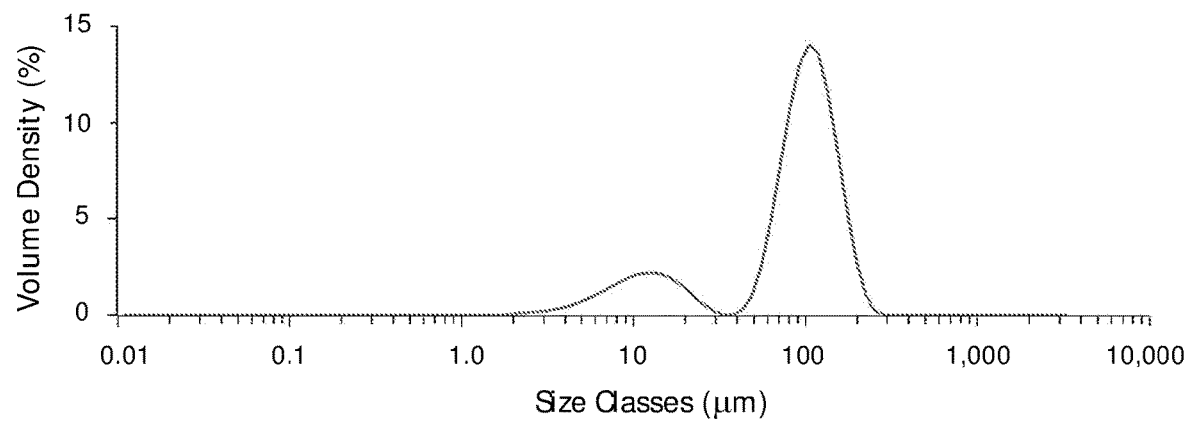
FIG. 5 shows the particle size distribution of the pharmaceutical composition of the embodiments (see Example 3). Two populations of the particles are clearly seen: the active agent (API) in the range of 5-25 microns (μm) and lactose in the range of 50-200 microns; D(10)=11.6 μm; D(50)=95.4 μm; D(90)=155 μm.
Figure 6:
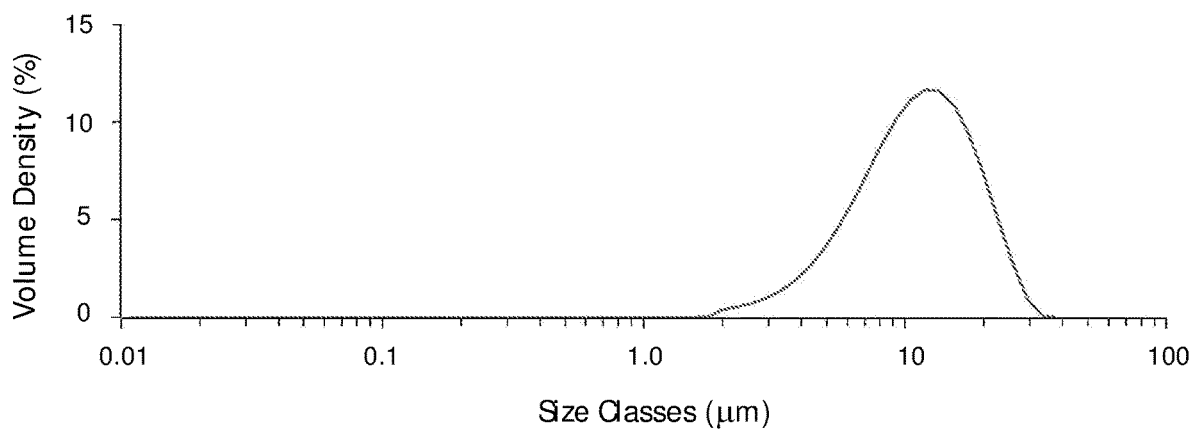
FIG. 6 shows the particle size distribution of the API in the pharmaceutical composition of the embodiments (see Example 3). The mean particles size is 12 μm.

The sumatriptan succinate composition prepared in Example 3 was subjected to the particle size analysis using the Malvern Laser Diffraction instrument (see FIGS. 5 and 6). The following particle size distribution was obtained for the sumatriptan succinate composition (see FIG. 5): D(10)=7 µm, D(50)=79 µm and D(90)=179 µm. Two populations of the particles are clearly seen in the figures. The 5-25 µm particles are sumatriptane succinate and the 50-200 µm particles are lactose monohydrate. The amount of the particles having the size less than 5 µm is about 1%. The particle size distribution of sumatriptan succinate alone was estimated in the range of 0-40 µm (see FIG. 6), and the following results were obtained: D(10)=5.2 µm, D(50)=11.2 µm, D(90)=20.1 µm and D(99)=27.1 µm.

Example 6

Acetaminophen (Paracetamol) Composition with Lactose Monohydrate

Acetaminophen (paracetamol) (2.3 g) was dissolved in 65 g ethanol under stirring at 300 rpm. An appropriate size magnetic bar was placed in the receiver and lactose monohydrate (2.3 g) was added there. The stirring rate was set at 150 rpm. The clear and homogeneous solution of the drug was spray-dried using the Büchi Mini Spray-Dryer with inlet air temperature of 105° C. and outlet temperature of 56° C., thereby obtaining the dry powder of paracetamol, which was further blended in-situ with lactose monohydrate. Stirring was being maintained during the entire process. Concentration of paracetamol in the composition was found to be 23% w/w.

Example 7

SEM Imaging of the Paracetamol Composition

The SEM images (not shown here) show that the small spherical particles of paracetamol having a narrow size distribution of 2-30 µm are dispersed between the large polyhedron particles of lactose ranging from 50 µm to 200 µm.

Example 8

Particle Size Analysis of the Paracetamol Composition

The paracetamol composition prepared in Example 6 was subjected to the particle size analysis using the Malvern Laser Diffraction instrument. The following particle size distribution was obtained: D(10)=11.6 µm, D(50)=95.4 µm and D(90)=155 µm. Two separate populations of the particles were clearly seen. The 2-30 µm particles are paracetamol and the 50-200 µm particles are lactose monohydrate. The percentage of the particles having the size less than 5 µm was about 7% w/w.

Example 9

Morphine Sulphate Composition with Lactose Monohydrate

Morphine sulphate (2.3 g) was dissolved in a mixture of 18.9 g ethanol and 13.9 g water under stirring at 300 rpm. An appropriate size magnetic bar was placed in the receiver and lactose monohydrate (2.3 g) was added there. The stirring rate was set at 150 rpm. The clear and homogeneous solution of the active agent was spray-dried using the Büchi Mini Spray-Dryer with inlet air temperature of 110° C. and outlet temperature of 86° C., thereby obtaining the dry powder of morphine sulphate, which was further blended in-situ with lactose monohydrate in the receiver. Stirring was being maintained during the entire process. Concentration of morphine sulphate in the composition was about 32% w/w and concentration of morphine base was about 28% w/w.

Example 10

Particle Size Analysis of the Morphine Sulphate Composition

The morphine sulphate composition prepared in Example 9 was subjected to the particle size analysis using the Malvern Laser Diffraction instrument. The following particle size distribution was obtained: D(10)=7.1 µm, D(50)=70.7 µm and D(90)=156 µm. The amount of the particles having the size less than 5 µm was about 6.6% w/w.

Example 11

Alprazolam Composition with Lactose Monohydrate

Alprazolam (2.3 g) was dissolved in 32.5 g of ethanol under stirring at 300 rpm. An appropriate size magnetic bar was placed in the receiver and lactose monohydrate (2.3 g) was added there. The stirring rate was set at 150 rpm. The obtained clear and homogeneous solution of the drug was then spray-dried using the Büchi Mini Spray-Dryer with inlet air temperature of 110° C. and outlet temperature of 86° C., thereby obtaining the dry powder of alprazolam, which was further blended in-situ with lactose monohydrate in the receiver. Stirring was being maintained during the entire process. Concentration of alprazolam in the composition was about 33% w/w.

Example 12

Particle Size Analysis of the Alprazolam Composition

The alprazolam—composition prepared in Example 11 was subjected to the particle size analysis using the Malvern Laser Diffraction instrument. The following particle size distribution was obtained: D(10)=11.7 µm, D(50)=88.0 µm and D(90)=187 µm. The amount of the particles having the size less than 5 µm was about 0.6% w/w.

Example 13

SEM Imaging of the Alprazolam Composition

Figure 7:
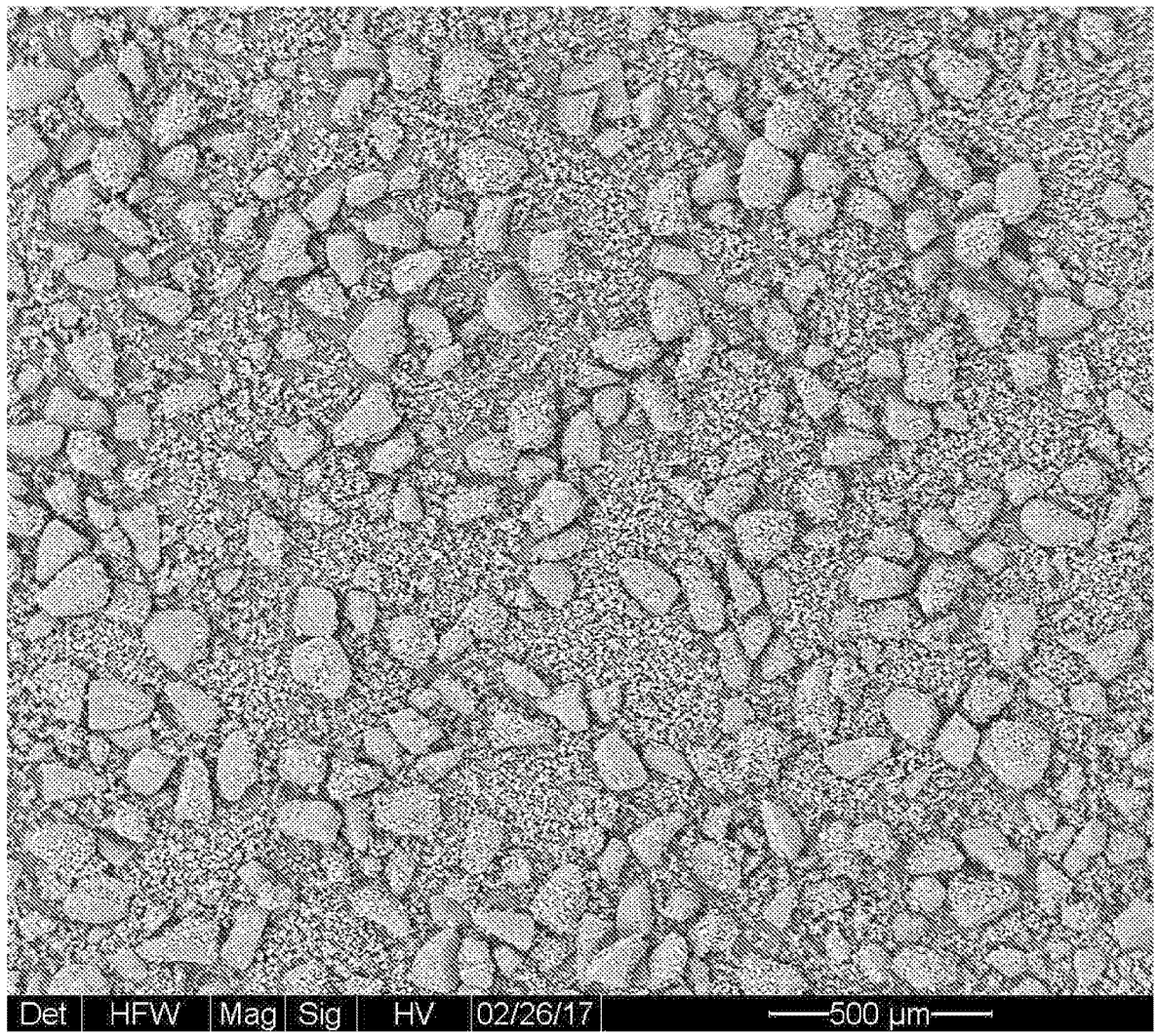
FIG. 7 shows the SEM image (X100) of the mixture of lactose monohydrate (large polyhedrons) and alprazolam in the dry powder composition of the embodiments for intranasal administration.

FIG. 7 shows the small polyhedron particles of alprazolam having the narrow size distribution of 5-40 µm, which are dispersed between the large polyhedron particles of lactose ranging from 50 µm to 200 µm. FIG. 8 shows an X-ray analysis of the obtained alprazolam polyhedron particles, where the large particles containing C and O atoms only must be lactose, and the small particles additionally containing Cl atoms must be alprazolam.

Example 14

Oxycodone Hydrochloride Composition with Lactose Monohydrate

Oxycodone hydrochloride (2.3 g) was dissolved in 9.9 g of ethanol under stirring at 300 rpm. An appropriate size magnetic bar was placed in the receiver and lactose monohydrate (2.3 g) was added there. The stirring rate was set at 150 rpm. The clear and homogeneous solution of the drug was spray-dried using the Büchi Mini Spray-Dryer with inlet air temperature of 90° C. and outlet temperature of 56° C., thereby obtaining the dry powder of the active agent, which was further blended in-situ with lactose monohydrate in the receiver. Stirring in the receiver was being maintained during the entire process. Concentration of oxycodone hydrochloride in the composition was about 41% w/w and concentration of oxycodone base was about 37% w/w.

Example 15

SEM Imaging of the Oxycodone Hydrochloride Composition

Figure 9:
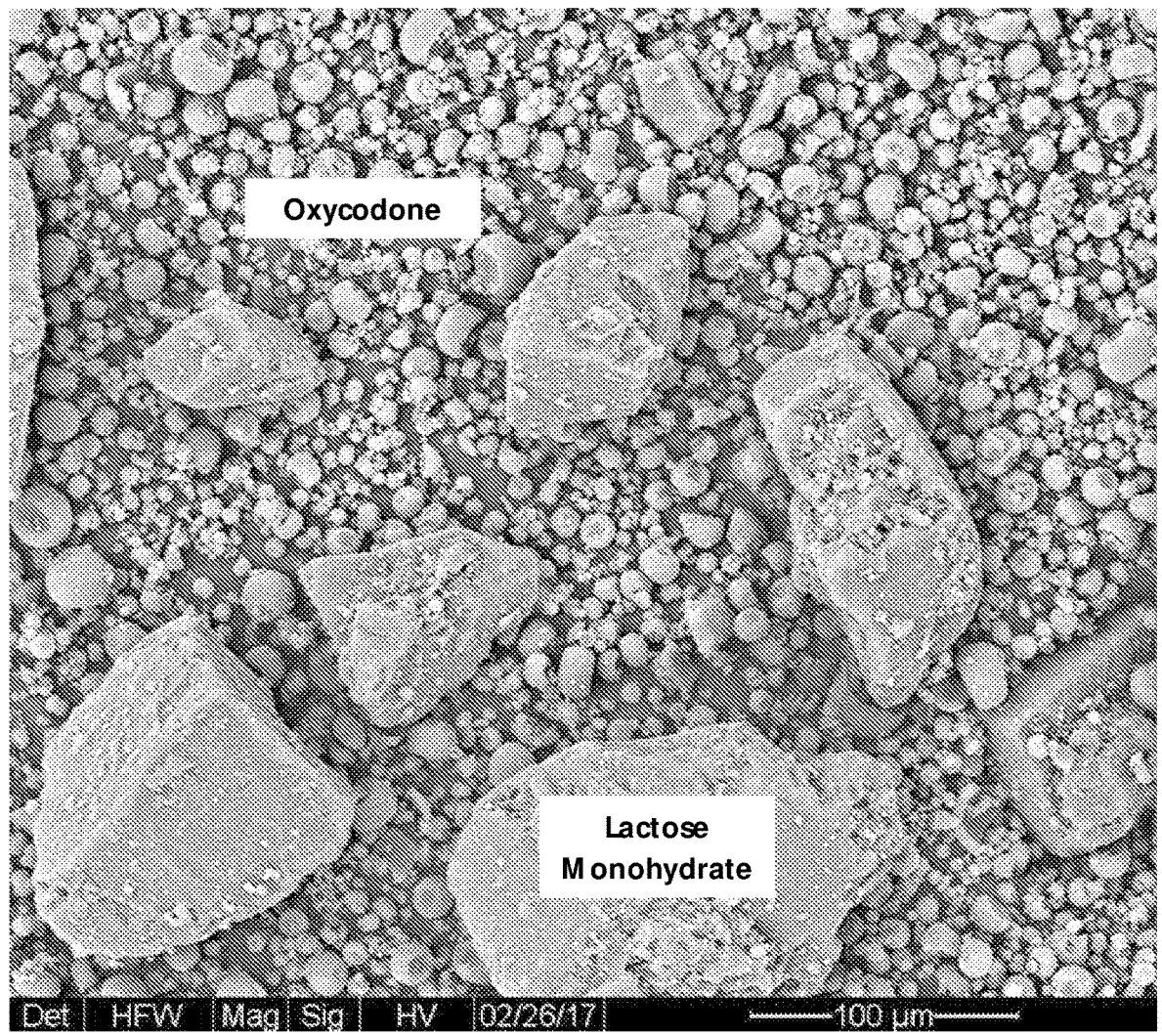
FIG. 9 shows the SEM images (X600) of the mixture of lactose monohydrate (large polyhedrons) and oxicodone hydrochloride (small non-aggregated spheres) in the dry powder composition of the embodiments for intranasal administration.

FIG. 9 shows the small spherical particles of oxycodone hydrochloride having the narrow size distribution of 3-30 µm, which are dispersed between the large polyhedron particles of lactose ranging from 50 µm to 200 µm.

Example 16

Particle Size Analysis of the Oxycodone Hydrochloride Composition

Figure 10:
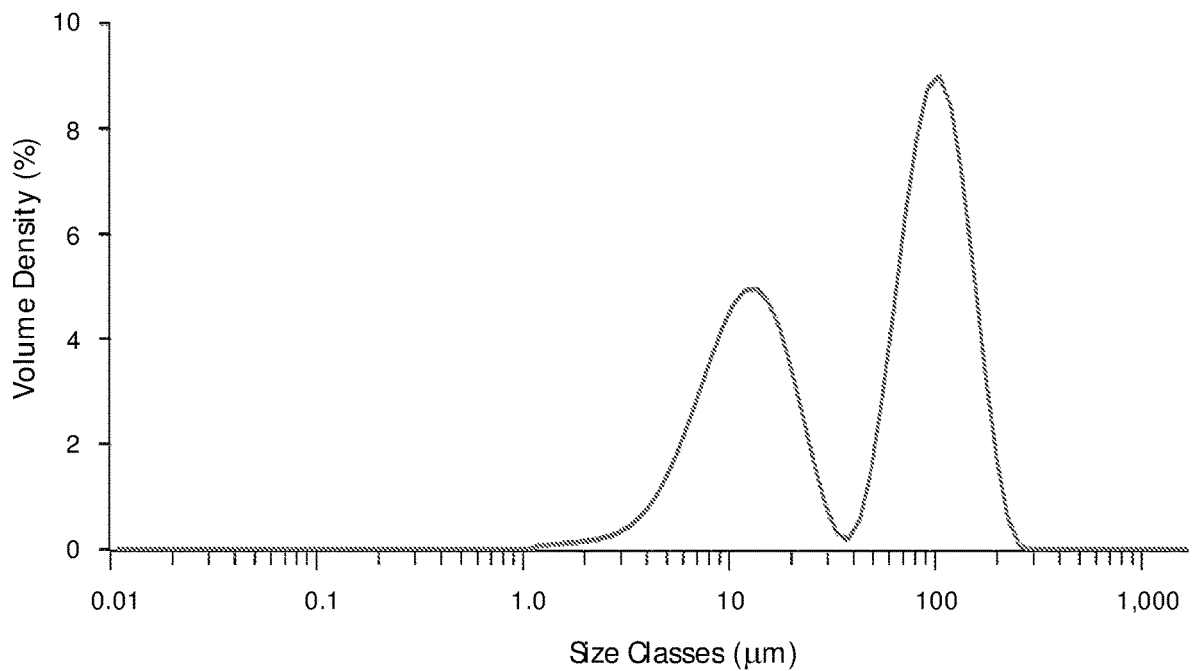
FIG. 10 shows the particle size distribution of the pharmaceutical composition of the embodiments (see Example 14). Two populations of particles is clearly seen: oxicodone hydrochloride in the range of 3-30 μm and lactose in the range of 50-200 μm. D(10)=57.4 μm; D(50)=97.3 μm; D(90)=151 μm.

The oxycodone hydrochloride composition prepared in Example 14 was subjected to the particle size analysis using the Malvern Laser Diffraction instrument (see FIG. 10). The following particle size distribution was obtained: D(10)=7.7 µm, D(50)=64.4 µm and D(90)=141 µm. The amount of the particles having the size less than 5 µm was about 3% w/w.

Example 17

Dopamine Hydrochloride Composition with Lactose Monohydrate

Dopamine hydrochloride (2.3 g) was dissolved in a mixture of 7.0 g ethanol, 7.0 g acetone and 9.0 g water under stirring at 300 rpm. An appropriate size magnetic bar was placed in the receiver and lactose monohydrate (2.3 g) was added there. The stirring rate was set at 150 rpm. The obtained clear and homogeneous solution of the active agent was spray-dried using the Büchi Mini Spray-Dryer with inlet air temperature of 95° C. and outlet temperature of 65° C., thereby obtaining the dry powder of dopamine hydrochloride, which was further blended in-situ with lactose monohydrate in the receiver. Stirring in the receiver was being maintained during the entire process. Concentration of dopamine hydrochloride in the composition was about 37% w/w and concentration of dopamine base was about 26% w/w.

Example 18

Particle Size Analysis of the Dopamine Hydrochloride Composition

The dopamine hydrochloride composition prepared in Example 17 was subjected to the particle size analysis using the Malvern Laser Diffraction instrument. The following particle size distribution was obtained: D(10)=8.0 µm, D(50) =74.9 µm and D(90)=147 µm. The amount of the particles having the size less than 5 µ was about 3.5% w/w.

Example 19

Insulin Composition with Lactose Monohydrate 5 ml of insulin saline (sodium chloride) solution containing 500 IU of insulin was mixed with 7 ml of water under stirring at 300 rpm. An appropriate size magnetic bar was placed in the receiver and lactose monohydrate (2.3 g) was added there. The stirring rate was set at 150 rpm. The obtained clear and homogeneous solution of insulin was spray-dried using the Büchi Mini Spray-Dryer with inlet air temperature of 90° C. and outlet temperature of 56° C., thereby obtaining the insulin dry powder, which was further blended in-situ with lactose monohydrate in the receiver. Stirring in the receiver was being maintained during the entire process.

Example 20

SEM Imaging of the Insulin Composition

Figure 11:
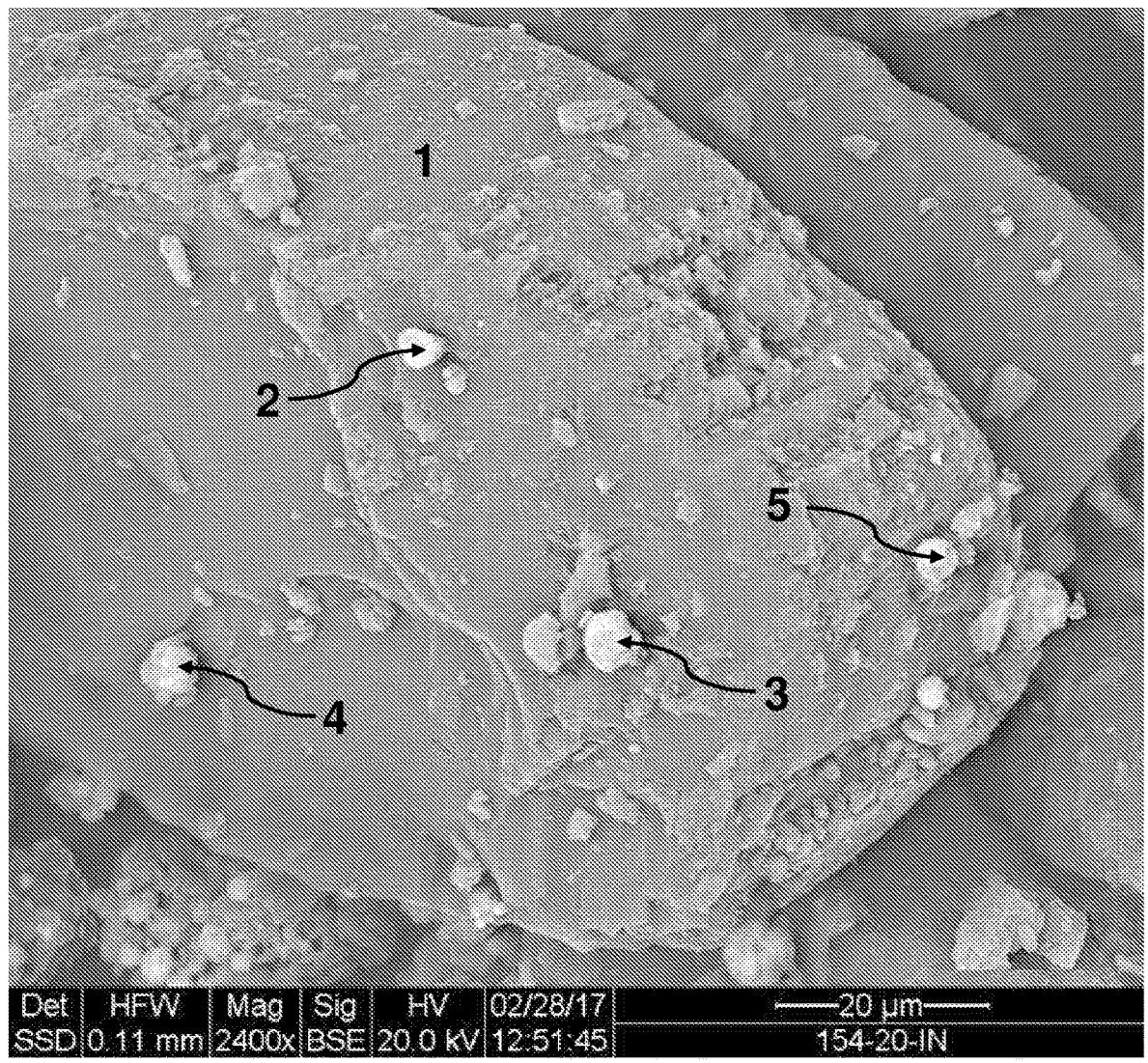
FIG. 11 shows the SEM image (X2400) of lactose monohydrate (large polyhedrons) (Particle 1) and insulin-sodium chloride (small spherical shape) (Particles 2, 3, 4 and 5) of the dry powder composition for intranasal administration.
Figure 12:
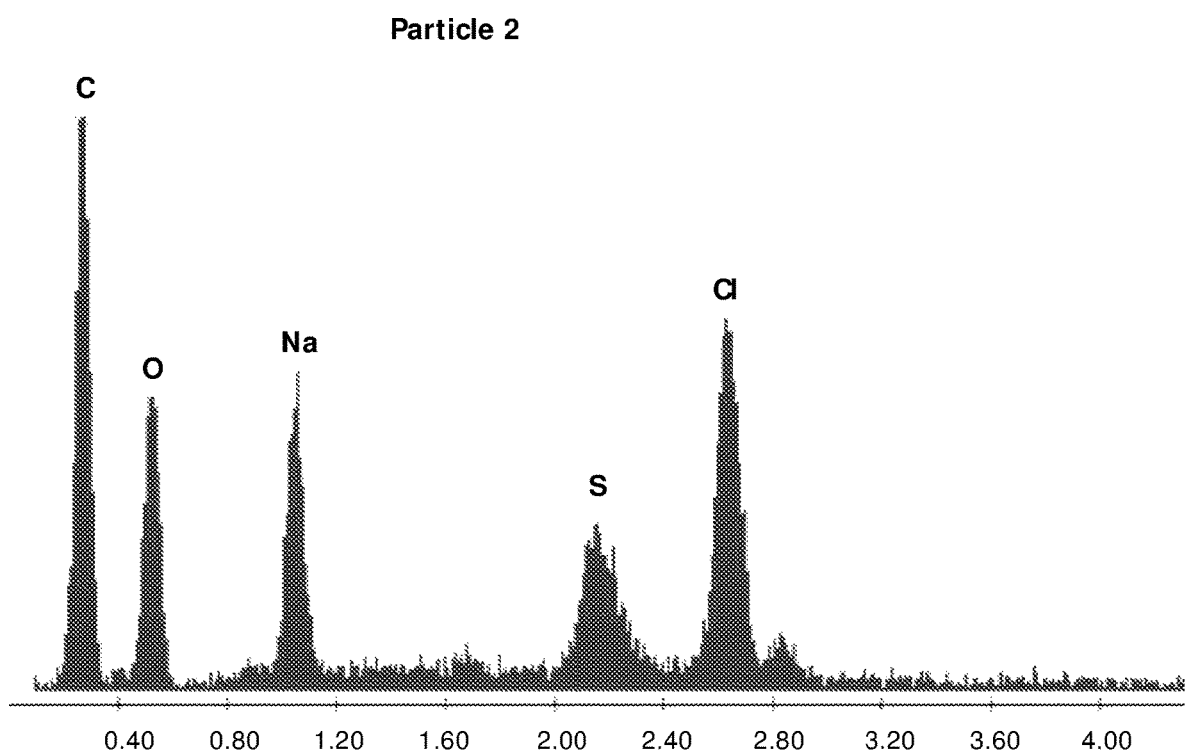
FIG. 12 shows the X-ray elemental analysis of Particle 2 containing "C", "O" and "S" atoms of insulin molecules and "Na" and "Cl" atoms of the sodium chloride salt.

FIG. 11 shows the small spherical particles of insulin-sodium chloride having the size of 5-7 µm laid on the surface of the large lactose polyhedron particles having the size above 100 µm. The elemental analysis shown on the FIG. 12 confirms that the particles include sodium chloride and sulphur, which is a clear indication that these particles are insulin.

Example 21

Particle Size Analysis of the Insulin Composition

Figure 13:
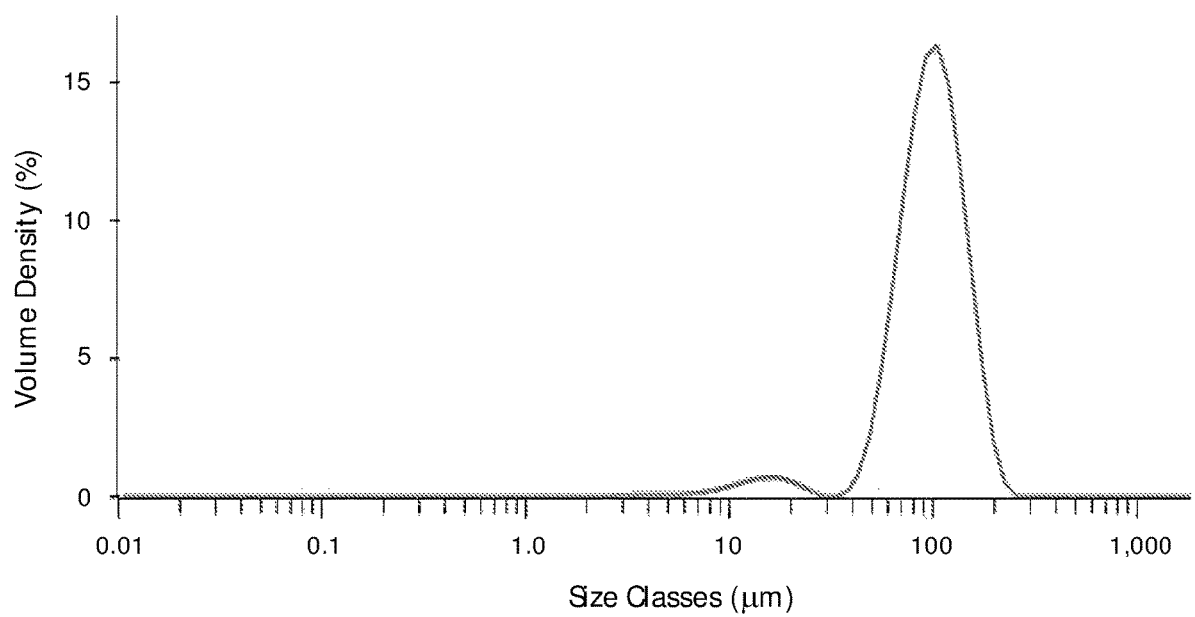
FIG. 13 shows the particle size distribution of the pharmaceutical composition of the embodiments (see Example 19). Two populations of the particles are clearly seen: insulin-sodium chloride particles in the range of 5-35 μm and lactose in the range of 50-200 μm. D(10)=57.4 μm; D(50)=97.3 μm; D(90)=151 μm.

The insulin composition prepared in Example 19 was subjected to the particle size analysis using the Malvern Laser Diffraction instrument. The following particle size distribution was obtained (see FIG. 13): D(10)=57.4 μm, D(50)=97.3 μm and D(90)=151 μm. The amount of the particles having the size less than 5 μm was about 0.3% w/w.

Example 22

Intranasal Drug Delivery

Aptar Unit-Dose Powder disposable devices were filled with the sumatriptan succinate composition prepared in Example 1. These devices were assembled according to the company guideline. Each device contained 10 mg of powder including 1 mg of sumatriptan succinate (100 mg/g as a labeled claim). Ten devices were packed, activated, and the powder delivered upon actuation of each device was collected and weighed. The weights (mg) of the delivered powder dose from the ten devices are shown in Table 1 below. Uniformity of the delivered dose (mg/g) from each of the ten devices, measured with an HPLC instrument according to the company protocol, is also shown in Table 1. In addition, Table 1 contains the data from the two devices that were stored for 6 months ("6M" in the table) at 40° C. and 75 RH.

TABLE 1

Delivered dose and uniformity of the delivered dose

| Sample name | Sample weight, mg | Sumatriptan base content, mg/g |
|---|---|---|
| Composition 1-1 | 10.04 | 103.40 |
| Composition 1-2 | 10.05 | 93.51 |
| Composition 1-3 | 10.07 | 108.63 |
| Composition 1-4 | 9.94 | 103.28 |
| Composition 1-5 | 10.07 | 91.54 |
| Composition 1-6 | 10.05 | 104.63 |
| Composition 1-7 | 10.04 | 99.15 |
| Composition 1-8 | 10.06 | 122.88 |
| Composition 1-9 | 10.03 | 109.75 |
| Composition 1-10 | 10.00 | 106.86 |
| AVG | 10.03 | 104.06 |
| RSD, % | 0.4 | 8.5 |
| Composition 1-11 (6M) | 9.79 | 97.42 |
| Composition 1-12 (6M) | 9.82 | 104.95 |
| AVG | 9.8 | 101.2 |
| RSD, % | 0.3 | 7.4 |

Example 23

Plume Geometry and Spray Pattern

Evaluation of the Plume Geometry and Spray Pattern of the compositions actuated from the Aptar Unit-Dose Powder (UDP) disposable devices was conducted using FDA's CMC Guidance[9]. Three replicates of each composition either fresh prepared or stored were tested for: Plume angle (°); Plume width at 6 cm; Plume length (cm) and duration time (ms). Results from two spray-patterns (3 and 6 cm) were recorded providing details on diameter min (cm), diameter max (cm), area and ovality ratio. An appropriate high-resolution visualisation technique was used.

[9] Nasal Spray and Inhalation Solution, Suspension, and Spray Drug Products—Chemistry, Manufacturing, and Controls Documentation, July 2002.

Example 24

PK Evaluation Following Single Intranasal or Oral Dose Administration of Oxycodone in Rats The objective of this study was to determine the pharmacokinetic profile of oxycodone following single administration of oral solution of oxycodone hydrochloride in PBS buffer and intranasal (IN) powder of oxycodone composition of invention described in the Example 14. The dosing was done at 10 mg/kg (2 mg per rat) by oral gavage or by modified intranasal Aptar device to 12 SD male rats for each rout of administration.

Study variables and end points were measured as following:
1) Morbidity and Mortality—daily.
2) Body weight—was measured during acclimation and before Test Item administrations.
3) Clinical sign observation—animals were observed for toxic signs after dosing.
4) Blood withdrawal—blood were collected at baseline (24 hours before dosing), 5, 15, 40, 60, 90, 120, 240 and 420 minutes after administration (three rats per bleeding time points for each Rout of administration).
5) Brains were removed after bleeding at time points: 15, 60, 120 and 420 minutes (three rats at each time point for each Rout of administration)

$T_{max}$, $C_{max}$ and $AUC_t$ (area under the concentration-time curve from zero up to a definite time t, the parameter that is used as an index of the drug exposure of the body, when referred to the plasma drug levels, and is closely dependent on the drug amount that enter into the systemic circulation).

The brain PK parameters were measured in the similar manner and reported as drug concentration in the ml of homogenated brain tissues. These samples were analysed for oxycodone content by a HPLC-UV method. The obtained plasma pharmacokinetic parameters of the oral and the intranasal products are shown in Table 2 and FIG. 14.

TABLE 2

Oxycodone pharmacokinetic parameters in rat's plasma

| Oxycodone Product | $AUC_{0-420}$ (μg * min/ml) | $T_{max}$ (min) | $C_{max}$ (μg/ml) | $C_{max\ IN}/C_{max\ ORAL}$ (%) | $AUC_{IN}/AUC_{ORAL}$ (%) |
|---|---|---|---|---|---|
| Intranasal powder | 4.23 | 5 | 1.88 | 2.98 | 1.49 |
| Oral gavage | 2.83 | 60 | 0.63 | | |

As can be seen from the Table 2 and FIG. 14, the $C_{max}$ value is almost 3 folds higher, while the AUS value is increased at 1.5 folds upon intranasal administration. The comparative value of $T_{max}$, of 5 min versus 60 min demonstrates the extremely fast onset of action following intranasal administration of oxycodone. The very fast nasal transmucosal absorption is manifested by the immediate increase in plasma oxycodone concentration, since it is observed following the administering of only the intranasal powder. The initial increase is later followed by the second peak of 60 min, exhibiting the gastrointestinal absorption, which is seen both in the intranasal and oral oxycodone formulations.

As the intranasal formulation has been reported to have a more rapid onset of effect[10,11], which is attributed to the rapid increase in blood levels, the present results suggest that oxycodone intranasal powder also has a fast pain relief onset of action.

[10] Mohammad Obaidi et al., Improved Pharmacokinetics of Sumatriptan with Breath Powered™ Nasal Delivery of Sumatriptan Powder, Headache, 2013, vol. 53, pp 1323-1333
[11] Fuseau E et al., Clinical pharmacokinetics of intranasal sumatriptan, Clin. Pharmacokinet., 2002, vol. 41(11), pp 801-811.

The obtained brain pharmacokinetic parameters of the oral and the intranasal products are shown in Table 3 and FIG. 15.

TABLE 3

Oxycodone pharmacokinetic parameters in rat's brain

| Oxycodone Product | $AUC_{0-420}$ (μg * min/ml) | $T_{max}$ (min) | $C_{max}$ (μg/ml) | $C_{max\,IN}/C_{max\,ORAL}$ (%) | $AUC_{IN}/AUC_{ORAL}$ (%) |
|---|---|---|---|---|---|
| Intranasal powder | 29.03 | 420 | 6.63 | 12.05 | 11.52 |
| Oral gavage | 2.52 | 120 | 0.55 | | |

As can be seen from the Table 3 and FIG. 15, the $C_{max}$ value is 12 folds higher, while the AUS value is increased 11.5 times upon intranasal administration. The $T_{max}$ value of 420 min versus 120 min demonstrates the sustained action of oxycodone following intranasal administration. However, the concentrations of the drug after 15 min were found to be 2.94 μg/ml and 0.23 μg/ml for intranasal and oral route, respectively. This is the clear evidence that the immediate and huge increase of oxycodone concentration in brain is a result of the direct drug delivery to the brain via intranasal route exclusively. The oxycodone peak in brain of 120 min following the gastrointestinal absorption is typical for oral oxycodone formulations.

The rapid onset and prolonged action of oxycodone demonstrated in the present application is a significant breakthrough in the post-surgery pain management of patients. Both oral and intranasal formulations were well tolerated. No toxic signals or any abnormal effects were observed.

The invention claimed is:

1. A pharmaceutical composition in a form of dry powder for intranasal administration to a patient in need thereof, consisting of solid particles consisting of at least one active agent and solid particles of a disaggregation agent, wherein at least 90% of the solid particles of said at least one active agent have a mean particle size ranging from 10 microns to 30 microns, and less than 10% of the solid particles of said at least one active agent have a mean particle size equal to or below 5 microns.

2. The pharmaceutical composition of claim 1, wherein the mean particles size of the solid particles of said disaggregation agent is 30-200 microns.

3. The pharmaceutical composition of claim 1, wherein the at least one active agent is selected from analgesics, anti-emetics, anti-inflammatory agents, anti-bacterial agents, anti-viral agents, anti-depressants, anti-epileptics, anti-hypertensive agents, anti-migraine agents, anti-neoplastic agents, chemotherapeutic drugs, immunosuppressants, anti-Parkinsonian agents, anxiolytic agents, sedatives, hypnotics, neuroleptics, beta-blockers, corticosteroids, COX-2 inhibitors, opioid analgesics, protease inhibitors, hormones, peptides, antibodies, chemotherapy agents and mixtures thereof.

4. The pharmaceutical composition of claim 3, wherein the at least one active agent is selected from sumatriptan succinate, zolmitriptan salts, naratriptan, rizatriptan, almotriptan, eletriptan, frovatriptan, bupivacaine, fibroblast growth factor, cephalexin, lidocaine, clobazame, midazolam, alprazolam, diazepine, lorazepam, dexmedetomidine, monosialoganglioside, cocaine, insulin, glucagon, oxytocin, fentanyl, sulfentanil, diamorphine, ketamine, apomorphine, buprenorphine, morphine sulphate, oxycodone hydrochloride, butorphanol, Non-Steroidal Anti-Inflammatory Drugs (NS AID), paracetamol, benzodiazepines, dopamine, pramipexole, rasagiline, rogitine, ondansetron, granisetron, metoclopramide, naloxone, naltrexone, atropine, adrenaline, cannabis active compounds, epinephrine, isosorbide dinitrate, obitoxine, dexmedetomidine, metochlorpramide, L-dopa, nicotine, sildenafil, nafarelin, dobutamine, phenylephrine, tramazoline, xylometazoline, tramadol, methacholine, ipratropium, scopolamine, propranolol, verapamil, hydralazine, nitroglycerin, clofilium tosylatecannabis active compounds and pharmaceutically acceptable salts, isomers, and mixtures thereof.

5. The pharmaceutical composition of claim 1, wherein the disaggregation agent is selected from lactose monohydrate, lactose, or a lactose functional analogue.

6. The pharmaceutical composition of claim 5, wherein the solid particles of said the disaggregation agent have a mean particle size of 30-200 microns.

7. The pharmaceutical composition of claim 6, wherein the solid particles of said the disaggregation agent have a mean particle size of 50-150 microns.

8. The pharmaceutical composition of claim 5, wherein the disaggregation agent is the lactose functional analogue and is selected from cellulose and derivatives, starch and derivatives, dextrose, sorbitol, mannitol, maltitol, xylitol, or mixtures thereof.

9. The pharmaceutical composition of claim 8, wherein the solid particles of said lactose functional analogue have a mean particle size of 50-150 microns.

10. The pharmaceutical composition of claim 1, wherein the solid particles of the active agent are of a substantially spherical form.

11. The pharmaceutical composition of claim 1 for use in intranasal administration to a patient in need thereof, wherein the administration is targeted at the uppermost region of the nasal cavity, thereby resulting in the nose-to-brain (N2B) delivery of the active agent to the brain of the patient.

12. The pharmaceutical composition of claim 1 for use in intranasal administration to a patient in need thereof, wherein the administration is targeted at the uppermost region of the nasal cavity, thereby resulting in transmucosal systemic administration.

13. An apparatus for preparation of the dry powder pharmaceutical composition of claim 1, said apparatus comprising:
- a) A spray-drying chamber configured for spray-drying a clear and homogeneous solution of at least one active agent to obtain solid particles of said at least one active agent in a moist air stream, said solution being free of any diluent or excipient;
- b) A cyclone separator configured for receiving said solid particles of said at least one active agent and the moist air stream from said spray-drying chamber, separating said solid particles of said at least one active agent from the moist air stream through vortex separation, exhausting the air and transferring the separated solid particles of said at least one active agent to a receiving chamber through a bag filter; and
- c) A receiving chamber pre-filled with solid particles of a disaggregation agent and configured for receiving the separated solid particles of said at least one active agent from the cyclone separator, mechanically stirring and homogenising said solid particles of said at least one active agent with the solid particles of the disaggregation agent to obtain the pharmaceutical composition in the dry powder form as defined in claim 1.

14. A method for preparation of the dry powder pharmaceutical composition as defined in claim 1, said method comprising:
- a) Preparing a clear and homogeneous solution of at least one active agent in an organic solvent or solvent mixture, in a solvent-water or water miscible solvent mixture, or in water, wherein said solution is free of any diluent or excipient,
- b) Providing a receiving chamber and filling the same with solid particles of disaggregation agent and continuously stirring the solid particles of disaggregation agent in the receiving chamber;
- c) Streaming the solution prepared in step (A) together with hot air to a spray-drying chamber, spray-drying the solution in the spray-drying chamber to obtain solid particles of said at least one active agent in a moist air stream, and transferring the obtained solid particles of said at least one active agent and the moist air stream to a cyclone separator;
- d) Separating said solid particles of said at least one active agent from the moist air stream through vortex separation in the cyclone separator, exhausting the air and transferring the separated solid particles of said at least one active agent to the receiving chamber through a bag filter;
- e) Stirring and homogenising said solid particles of said at least one active agent received from step (D) with the solid particles of the disaggregation agent in the receiving chamber to obtain the dry powder pharmaceutical composition in dry powder form; and
- f) Adding solid particles of the disaggregation agent to the dry powder pharmaceutical composition obtained in step (E) and mixing to obtain a desired active agent-to-disaggregation agent ratio in said dry powder pharmaceutical composition.

* * * * *